US012765821B2

(12) United States Patent
Munoz et al.

(10) Patent No.: US 12,765,821 B2
(45) Date of Patent: Oct. 20, 2026

(54) METHODS AND APPARATUS FOR DETECTING BRAIN DISORDERS

(71) Applicant: Queen's University at Kingston, Kingston (CA)

(72) Inventors: Douglas P. Munoz, Kingston (CA); Donald Christopher Brien, Selby (CA); Brian Charles Coe, Kingston (CA); Brian Joseph White, Amherstview (CA)

(73) Assignee: Queen's University at Kingston, Kingston (CA)

( * ) Notice: Subject to any disclaimer, the term of this patent is extended or adjusted under 35 U.S.C. 154(b) by 291 days.

(21) Appl. No.: 18/561,400

(22) PCT Filed: May 18, 2022

(86) PCT No.: PCT/CA2022/050784

§ 371 (c)(1),
(2) Date: Nov. 16, 2023

(87) PCT Pub. No.: WO2022/241554

PCT Pub. Date: Nov. 24, 2022

(65) Prior Publication Data

US 2024/0366131 A1 Nov. 7, 2024

Related U.S. Application Data

(60) Provisional application No. 63/189,819, filed on May 18, 2021.

(51) Int. Cl.
*A61B 5/16* (2006.01)
*A61B 3/00* (2006.01)
(Continued)

(52) U.S. Cl.
CPC ............ *A61B 5/163* (2017.08); *A61B 3/0091* (2013.01); *A61B 3/11* (2013.01); *A61B 3/113* (2013.01); *A61B 5/7264* (2013.01)

(58) Field of Classification Search
CPC ......... A61B 5/163; A61B 3/0091; A61B 3/11; A61B 3/113; A61B 5/7264; A61B 5/4088
See application file for complete search history.

(56) References Cited

U.S. PATENT DOCUMENTS 9,629,543 B2 4/2017 Agichtein et al.
9,895,100 B2 * 2/2018 Port ...................... A61B 3/113
(Continued)

FOREIGN PATENT DOCUMENTS

KR 1020210052043 5/2021
WO WO2014/159498 A2 10/2014
(Continued)

OTHER PUBLICATIONS

International Search Report and Written Opinion for corresponding international Application No. PCT/CA2022/050784 filed May 18, 2022.

(Continued)

*Primary Examiner* — Eric F Winakur
(74) *Attorney, Agent, or Firm* — Stephen J. Scribner

(57) ABSTRACT

Apparatus and methods for detecting a brain disorder in a subject include a display device and an eye tracker operatively connected to a processor, wherein the display device displays visual scenes to the subject according to at least one viewing task. The eye tracker tracks at least one of the subject's eyes while the subject performs the viewing task, and outputs eye tracking data. The processor extracts data for one or more selected feature, and analyzes the data for the one or more selected feature using a classifier to determine one or more condition, validates the determined con- (Continued)

dition through comparisons to meta-data and the true condition if available, and generates an output based on the determined condition for the selected feature; wherein the output indicates the likelihood of the subject having a brain disorder.

22 Claims, 16 Drawing Sheets

(51) Int. Cl.

| | |
|---|---|
| ***A61B 3/11*** | (2006.01) |
| ***A61B 3/113*** | (2006.01) |
| ***A61B 5/00*** | (2006.01) |

(56) References Cited

U.S. PATENT DOCUMENTS

| | | | | |
|---|---|---|---|---|
| 9,962,119 | B2 * | 5/2018 | Macknik ................ | A61B 3/113 |
| 10,176,299 | B2 | 1/2019 | Torres et al. | |
| 10,413,176 | B2 * | 9/2019 | Mori ...................... | A61B 3/113 |
| 10,575,726 | B2 | 3/2020 | Wetzel et al. | |
| 11,503,998 | B1 | 11/2022 | De Villers-Sidani | |
| 2010/0208205 | A1 * | 8/2010 | Tseng ..................... | A61B 3/113<br>351/209 |
| 2012/0059282 | A1 * | 3/2012 | Agichtein ............. | A61B 3/113<br>600/587 |
| 2014/0364761 | A1 | 12/2014 | Benson et al. | |
| 2016/0022137 | A1 | 1/2016 | Wezel et al. | |
| 2016/0106315 | A1 | 4/2016 | Kempinski | |
| 2017/0112427 | A1 | 4/2017 | Simon et al. | |
| 2017/0308654 | A1 | 10/2017 | Luz Rello-Sanchez et al. | |
| 2021/0174959 | A1 | 6/2021 | Abel Fernandez | |

FOREIGN PATENT DOCUMENTS

| | | | |
|---|---|---|---|
| WO | 2014193564 | A1 | 12/2014 |
| WO | 2020188633 | A1 | 9/2020 |

OTHER PUBLICATIONS

Lagun, D., et al., "Detecting cognitive impairment by eye movement analysis using automatic classification algorithms", J Neurosci Methods. Author manuscript; available in PMC, pp. 1-21, (2012).

Al Dahhan, N. Z., et al., "Examining the neural and cognitive processes that underlie reading", Eur J Neurosci. 51: pp. 2277-2298, (2020).

Al Dahhan, N., et al., "Eye movements and articulations during a letter naming speed task: children with and without dyslexia", J. Learn. Disabilities 50: pp. 275-285, (2017).

Calancie OG, et al., "Maturation of temporal saccade prediction from childhood to adulthood: predictive saccades, reduced pupil size and blink synchronization". J Neurosci. 42: pp. 69-80, (2022).

Cos, B.C., et al., Automated Analysis Pipeline For Extracting Saccade, Pupil, and Blink Parameters Using Video-Based Eye Tracking. bioRxiv, (2022).

Filzmoser, P., et al, Outlier identification in high dimensions. Computational Statistics and Data Analysis, 52: pp. 1694-1711. (2008).

Habibi, M., et al. "Eye tracking identities biomarkers in α-synucleinopathies versus progressive supranuclear palsy", J. Neurology, https://link.springer.com/article/10.1007/s00415-022-11136-5, (2022).

Itti I. , Koch C., "Computational modelling of visual attention", Nat Rev Neurosci, 2: pp. 194-203, (2001).

Perkins, J.E., et al. "Sccade, Pupil, and Blink Responses in Rapid Eye Movement Sleep Behavior Disorder", Movement Disorders : Official Journal of the Movement Disorder Society, 36(7): pp. 1720-1726, (2021).

Peters, R.J., et al., "Components of bottom-up gaze allocation in natural images", Vision Research, 45: pp. 2397-2416, (2005).

Tseng, P.H., et al., "Hithroughout classification of clinical populations from natural viewing eye movements", J. Neurology, 260:275-284, (2013).

Vaca-Palomares, I., et al., "Voluntary saccade inhibition deficits correlate with extended white-matter cortico-basal atrophy in Huntington's disease", Neuroimage:Clinical, 15: pp. 502-512, (2017).

Van der Maaten, L.J.P. et al., "Visual tensional Data Using t-SNE", Journal of Machine Learning Research 9: pp. 2579-2605, (2008).

Wang, CA., et al., "Disruption of pupil size modulation correlates with voluntary motor preparation deflicts in Parkinson's disease", Neuropsychologia, 80: pp. 176-184, (2016).

Yep. R., et al. "Interleaved pro/anti-sccade behavior across the lifespan", Front. Aging Neurosci. (in press). (2022).

Extended European Search Report dated Feb. 25, 2025 for corresponding European Application No. EP 22803505.

Examination Report issued May 5, 2026 for corresponding Indian Patent Application No. 202347077869.

European Communication dated May 28, 2026 for corresponding European Patent Application No. 22 803 505.1.

Notice of Reasons for Rejection for corresponding Japanese Patent Application No. 2023-571473 dispatched Mar. 9, 2026.

* cited by examiner

Pipeline Analysis

↓

Data Cleaning / Imputation / Outlier Rejection

↓

Basic Features – Age, Sex, Reaction Times, Error Rates, Metrics, ...

↓

Functional Data – SRT, Microsaccades, Blinks, Pupil, Raw Eye Tracking Data

↓

Concatenation of all Features – Cross Validation via weighted Support Vector Machine with Feature Refinement

STRUCTURED: Interleaved Pro/Anti Saccade Task (IPAST)

Sub-groups

| Group | Fix Break | Pro SRT | Pro Express | Anti SRT | Exp Anti Error | Reg Anti Error | Pupil Baseline | Pupil Constrict | Pupil Dilate | Blinks |
|---|---|---|---|---|---|---|---|---|---|---|
| CVD | ↑ | - | - | ↑↑ | ↑ | ↑↑ | ↓ | ↓↓ | ↓↓ | - |
| bvFTD | ↑ | - | ↑ | ↑↑↑ | ↑↑ | ↑↑↑ | ↓ | ↓↓ | ↓↓ | ↓ |
| ALS | ↑ | ↓ | ↑ | - | - | ↑↑ | - | ↓↓ | - | - |
| AD/MCI | ↑ | ↓ | ↑ | ↑↑ | ↑ | ↑↑ | ↓ | ↓↓ | ↓↓ | - |
| PARK | ↑ | ↓ | ↑ | ↑↑ | ↑ | ↑↑ | - | ↓↓ | ↓↓ | ↓↓ |
| LRRK2 | ↑ | - | ↑ | - | - | ↑ | ↓ | ↓↓ | ↓ | - |
| RBD | - | - | - | - | - | - | - | ↓↓ | ↓↓ | ↓ |
| PSP | ↑ | ↑ | - | ↑↑↑ | ↑↑ | ↑↑↑ | ↓↓↓ | ↓↓↓ | ↓↓↓ | ↓↓ |
| HUNT | ↑↑ | ↑ | - | ↑↑↑ | - | ↑↑↑ | ↓ | ↓ | ↓ | - |

CVD: cerebrovascular disease; bvFTD: behavioural variant frontotemporal dementia; ALS: amyotrophic lateral sclerosis; AD: Alzheimer's disease; MCI: mild cognitive impairment; PARK: Parkinson's disease; LRRK2: LRRK2 gene mutation carriers; RBD: Rapid Eye Movement sleep behaviour disorder; PSP: progressive supranuclear palsy; HUNT: Huntington's disease.
Pro: pro-saccade task; Anti: anti-saccade task; SRT: saccadic reaction time; Express: express saccades; Exp: express saccades; Reg: regular latency saccades.
Arrows indicate direction of change from controls (up: increase; down: decrease; dash: no change).
The number of arrows indicate the magnitude of the effect.

Fig. 16

UNSTRUCTURED: Free Viewing

Sub-groups

| Group | Main Seq | Sacc Rebound | Sacc Rate | µsacc Inhib | µsacc Rate | Pupil Baseline | Pupil Sensitivity | Pupil Constrict | Pupil Dilate | Blink Rate | Blink Inhib |
|---|---|---|---|---|---|---|---|---|---|---|---|
| CVD | - | ↓ | ↓ | ↓ | - | - | - | ↓ | ↓ | ↑ | ↓ |
| bvFTD | - | ↓ | ↓ | - | - | ↓ | ↓ | ↓ | ↓ | ↑↑ | - |
| ALS | ↓ | - | - | ↓ | ↑ | ↑ | ↓ | ↓ | ↓ | - | ↑ |
| MCI | - | ↓ | ↓ | ↓ | ↑ | ↓ | ↓ | ↓ | ↓ | ↑ | - |
| AD | - | ↓↓ | ↓ | ↓ | ↑ | ↓↓ | ↓↓ | ↓↓ | ↓↓ | ↑↑ | - |
| PARK | ↓ | ↓↓ | ↓↓ | ↓ | ↑ | ↑ | ↑ | ↑ | ↑ | ↑ | ↑ |
| MSA | - | ↓ | ↓↓ | ↓↓ | ↑ | ↑↑ | ↑ | ↑↑ | ↑↑ | ↑ | ↑ |
| RBD | - | ↓ | - | ↓ | - | - | - | - | - | - | - |
| PSP | ↓↓ | ↓↓ | ↓↓ | ↓↓ | ↑ | ↓↓ | ↓↓ | ↓ | ↓ | ↓ | ↓ |
| HUNT | ↓ | ↓ | - | - | - | ↑↑ | ↑ | ↑↑ | ↑↑ | ↑↑ | ↑ |

CVD: cerebrovascular disease; bvFTD: behavioural variant frontotemporal dementia; ALS: amyotrophic lateral sclerosis; AD: Alzheimer's disease; MCI: mild cognitive impairment; PARK: Parkinson's disease; MSA: multiple system atrophy; RBD: Rapid Eye Movement sleep behaviour disorder; PSP: progressive supranuclear palsy; HUNT: Huntington's disease.

Main Seq: main sequence; Sacc Rebound: saccade rebound; Sacc rate: saccade rate; µsacc inhib: microsaccade inhibition; µsacc rate: microsaccade rate; Blink inhib: blink inhibition.

Arrows indicate direction of change from controls (up: increase; down: decrease; dash: no change). The number of arrows indicate the magnitude of the effect.

Fig. 17

METHODS AND APPARATUS FOR DETECTING BRAIN DISORDERS

FIELD

This invention relates to the detection and diagnosis of brain disorders in subjects by monitoring eye behaviour during viewing tasks. More specifically, the invention relates to detecting and diagnosing brain disorders by selecting and analyzing features of eye behaviour of subjects during viewing tasks.

BACKGROUND

Current approaches for detecting brain disorders based on eye tracking during viewing tasks (e.g., Perkins et al. 2021, Tseng et al. 2013) suffer from limitations including low participant intake, expensive equipment, the need for highly trained individuals, and slow analysis turn-over. In addition, current approaches (e.g., Coe et al. 2022) are prone to data loss, due in part to similar treatment of behavioral loss and tracking loss, resulting in loss of critical information relating to eye blinks and saccades.

SUMMARY

According to one aspect of the invention there is provided apparatus for detecting, diagnosing, and/or assessing a brain disorder in a subject, comprising: a display device and an eye tracker operatively connected to a processor; wherein the display device displays visual scenes to the subject according to at least one of a structured viewing task and unstructured viewing; wherein the eye tracker tracks at least one of the subject's eyes while the subject performs the structured viewing task and/or unstructured viewing, and outputs eye tracking data; wherein the processor receives the eye tracking data, extracts data for a plurality of selected features, and analyzes the data for the plurality of selected features; wherein the processor analyzes data for each of the selected features using a classifier to determine a condition, validates the determined conditions, and generates an output based on the determined conditions for the selected features; wherein the output indicates the likelihood of the subject having the brain disorder.

According to another aspect of the invention there is provided apparatus for detecting, diagnosing, and/or assessing a brain disorder in a subject, comprising: a display device and an eye tracker operatively connected to a processor; wherein the display device displays visual scenes to the subject according to at least one viewing task; wherein the eye tracker tracks at least one of the subject's eyes during the at least one viewing task and outputs eye tracking data; wherein the processor receives the eye tracking data, extracts data for one or more selected feature, and analyzes the data for the one or more selected feature; wherein the processor analyzes data for the one or more selected feature using a classifier to determine a condition, and generates an output based on the determined condition for the one or more selected feature; wherein the output indicates the likelihood of the subject having a brain disorder.

According to another aspect of the invention there is provided a method for detecting, diagnosing, and/or assessing a brain disorder in a subject, comprising: using an eye tracker to track at least one of the subject's eyes while the subject performs at least one of a structured viewing task and an unstructured viewing, and output eye tracking data; using a processor to receive the eye tracking data, extract data for a plurality of selected features, and analyze the data for the plurality of selected features; wherein the processor analyzes data for each of the selected features using a classifier to determine a condition, validates the determined conditions, and generates an output based on the determined conditions for the selected features; wherein the output indicates the likelihood of the subject having the brain disorder.

According to another aspect of the invention there is provided a method for detecting, diagnosing, and/or assessing a brain disorder in a subject, comprising: using an eye tracker to track at least one of the subject's eyes while the subject performs at least one viewing task, and output eye tracking data; using a processor to receive the eye tracking data, extract data for one or more selected feature, and analyze the data for the one or more selected feature; wherein the processor analyzes data for the one or more selected feature using a classifier to determine a condition and generates an output based on the determined condition for the one or more selected feature; wherein the output indicates the likelihood of the subject having a brain disorder.

Some embodiments may include validating the determined condition(s) through comparisons to metadata and a true condition. In some embodiments, validating the determined condition(s) may be omitted.

According to some embodiments, the structured viewing task may comprise a pro-saccade task and/or an anti-saccade task.

According to some embodiments, unstructured viewing may comprise a free viewing task.

According to some embodiments, unstructured viewing may comprise free viewing of video clips.

According to some embodiments, the display device may display a user interface to the subject.

According to some embodiments, the selected measures may comprise eye movement, eye blink, and pupil behaviour and coordination or interaction between them.

According to some embodiments, the eye movement may comprise saccades.

According to some embodiments, the eye movement may comprise saccades and smooth pursuit.

According to some embodiments, the classifier may be implemented with a machine learning model.

According to some embodiments, the machine learning model may comprise a support vector machine.

According to some embodiments, the brain disorder may comprise at least one of a neurodegenerative disease, a neuro-developmental disorder, a neuro-atypical disorder, a psychiatric disorder, and brain damage.

According to some embodiments, the brain disorder may comprises at least one of mild cognitive impairment, amyotrophic lateral sclerosis, frontotemporal dementia, progressive supranuclear palsy, Lewy Body Dementia Spectrum, Parkinson's Disease, Alzheimer's Disease, Huntington's Disease, rapid eye movement (REM) sleep behaviour disorder, multiple system atrophy, essential tremor, vascular cognitive impairment, fetal alcohol spectrum syndrome, attention deficit hyperactivity disorder, Tourette's Syndrome, autism spectrum disorders, opsoclonus myoclonus ataxia syndrome, optic neuritis, adrenoleukodystrophy, multiple sclerosis, major depressive disorders, bipolar, an eating disorder selected from anorexia and bulimia, dyslexia, borderline personality disorder, alcohol use disorder, anxiety, neuroCOVID disorder, schizophrenia, and apnea.

BRIEF DESCRIPTION OF THE DRAWINGS

For a greater understanding of the invention, and to show more clearly how it may be carried into effect, embodiments will be described, by way of example, with reference to the accompanying drawings, wherein:

FIG. 16 is a table of oculomotor deficits found in a variety of patient groups while performing structured viewing tasks. The number of arrows indicate magnitude of difference from control participants while the direction of the arrows indicates the direction of the difference (up, increase; down, decrease; dash, no change).

FIG. 17 is a table of oculomotor deficits found in a variety of patient groups while performing unstructured viewing tasks. The number of arrows indicate magnitude of difference from control participants while the direction of the arrows indicates the direction of the difference (up, increase; down, decrease; dash, no change).

DETAILED DESCRIPTION OF EMBODIMENTS

Described herein are apparatus and methods for detecting a brain disorder in a subject. As used herein, the term "detecting" may also refer to diagnosing and/or assessing a brain disorder. As used herein, the term "brain disorder" refers to any disorder in brain function that may result from one or more of, but not limited to, a neurodegenerative disease, a neuro-developmental disorder, a neuro-atypical disorder, a psychiatric disorder, or brain damage (stroke, ischemia, trauma, concussion, etc.), brain cancer, epilepsy, seizure, etc. Examples include, but are not limited to, mild cognitive impairment, amyotrophic lateral sclerosis, frontotemporal dementia, progressive supranuclear palsy, Lewy Body Dementia Spectrum, Parkinson's Disease, Alzheimer's Disease, Huntington's Disease, rapid eye movement (REM) sleep behaviour disorder, multiple system atrophy, essential tremor, vascular cognitive impairment, fetal alcohol spectrum syndrome, attention deficit hyperactivity disorder (all types), Tourette's Syndrome, autism spectrum disorders, opsoclonus myoclonus ataxia syndrome, optic neuritis, adrenoleukodystrophy, multiple sclerosis, major depressive disorders, bipolar, eating disorders (anorexia, bulimia, etc.), dyslexia, borderline personality disorder, alcohol use disorder, anxiety, neuroCOVID disorder, schizophrenia, and apnea.

Prior approaches for detecting brain disorders based on eye tracking during viewing tasks suffer from limitations including low participant intake, due in part to inconveniences involved in testing, expensive equipment, the need for highly trained individuals, and slow analysis turn-over. In addition, prior approaches are prone to data loss, due in part to similar treatment of behavioral loss and tracking loss. Embodiments described herein overcome such limitations by providing testing platforms that are easy and convenient for participants to use and include methods for cleaning/processing data without loss of critical data and identifying and selecting features for analysis. For example, embodiments herein provide methods and algorithms that treat eye blinks as features rather than simply a type of data loss, and extract critical information by specifically isolating data loss due to eye blinks vs data lost for other reasons. As a further example, embodiments herein provide methods and algorithms that address problems with the detection of eye saccade end point which has been problematic in prior approaches using data from video-based eye trackers. Embodiments provide task-based processing that enables accurate categorization of eye movement behavior in both structured tasks and unstructured viewing, and result in a stronger, more robust, learning machine.

Figure 1A:
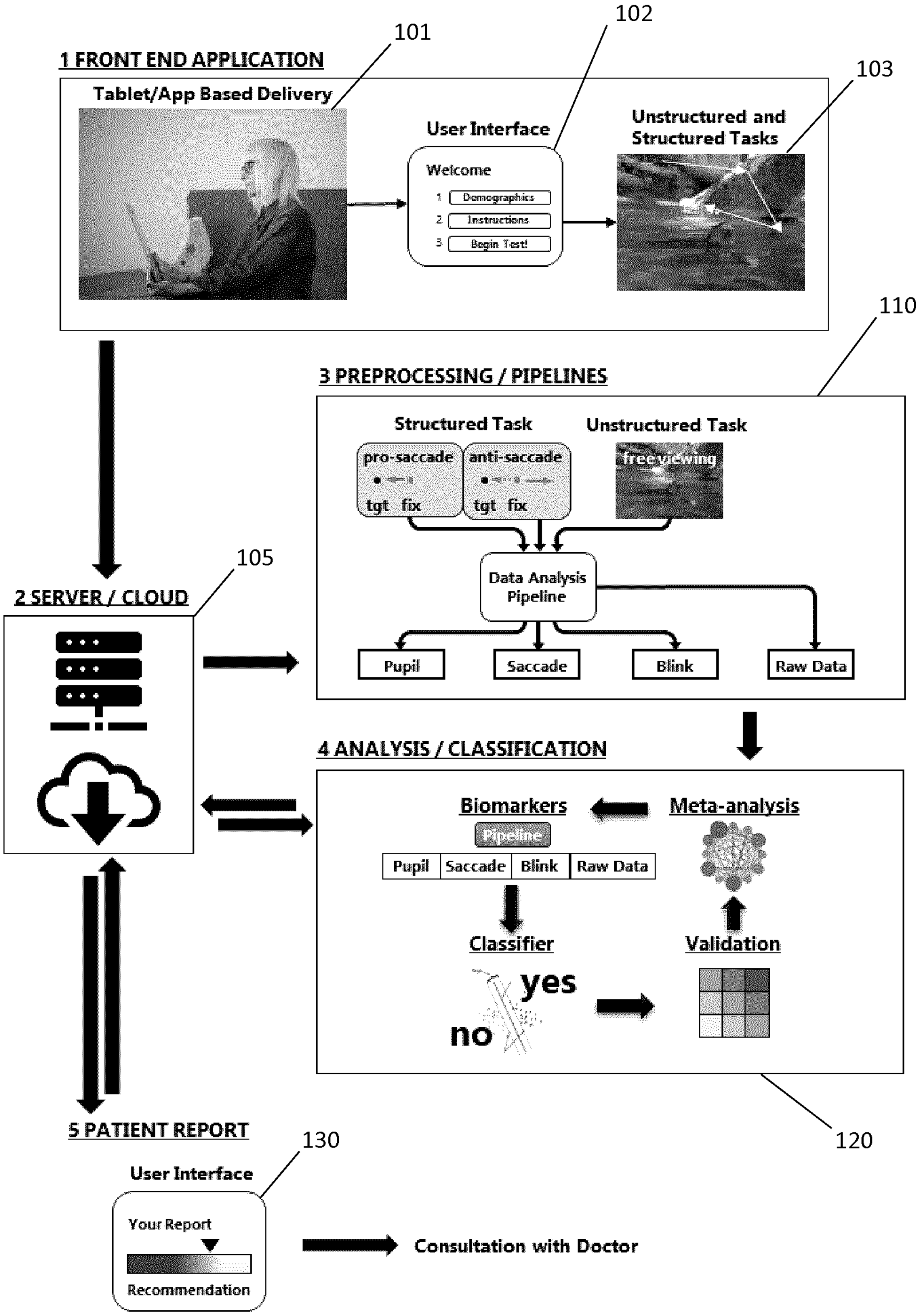
FIGS. 1A and 1B are diagrams showing process flow based on apparatus and methods for detecting, diagnosing, and/or assessing a brain disorder in a subject, according to embodiments.
Figure 1B:
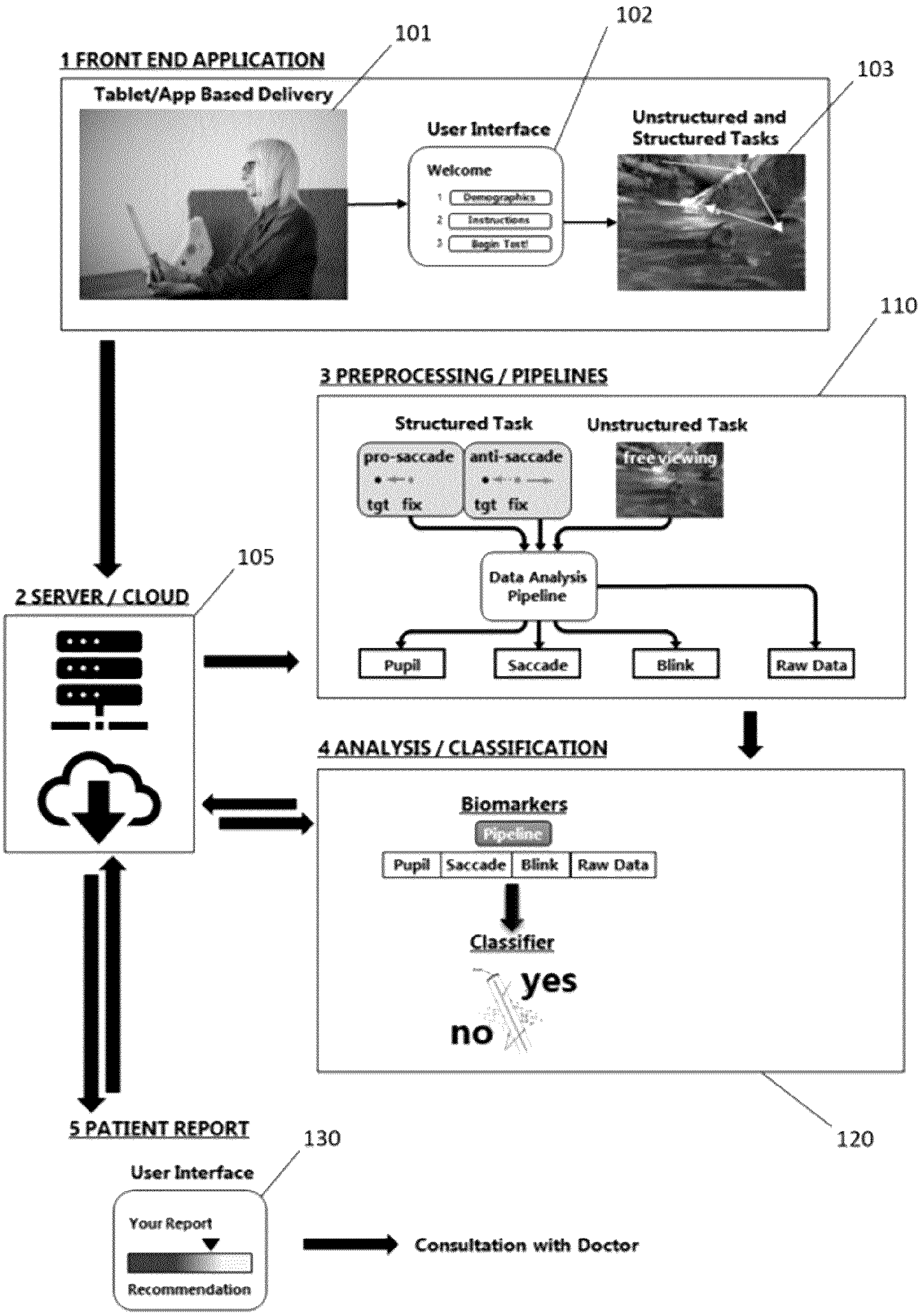

FIG. 1A shows features and process flow according to generalized apparatus and methods for detecting a brain disorder as described herein. This description provides embodiments of methods and apparatus which may include all of the features generally shown in FIG. 1A, or some of the features shown in FIG. 1A, e.g., FIG. 1B. It will be understood that FIGS. 1A and 1B present general overviews and are not limiting; that is, other features may be included in embodiments, or some features shown may not be included in embodiments.

Referring to FIG. 1A, at 101, a subject is presented with visual scenes displayed using a computer monitor, laptop computer, tablet, smart phone, a projected display, a wearable display, a hologram, a VR or AR display, etc., generally referred to herein as a "display", and an eye tracker (not shown) tracks behaviour of at least one of the subject's eyes. As used herein, the term "eye tracker" includes hardware that may be used to track a subject's eyes, such as a camera (e.g., a built-in camera of a laptop computer, smart phone, or tablet), a camera connected to a device, an eye tracking system, wearable eye tracking glasses or headset, etc., whether video based, laser based, etc. The presentation of visual scenes may be via a software application running on a device connected to the display, such as local computer, or a remote server, or running on a device integral with the display (e.g., a laptop computer, smart phone, or tablet). The software application may include a user interface 102 that provides information and instructions to the subject, prompts the subject to enter information, etc. The visual scenes 103 may include structured viewing tasks and/or unstructured viewing tasks, described in detail below. The device may optionally be connected to the internet and to remote servers, the cloud, etc., 105, for storing subject information, eye tracking data, etc.

A change in the visual scene 103 presented to the subject, which may be implemented as a structured viewing task and/or an unstructured viewing task, results in a visual perturbation that sweeps through the visual areas of the brain and alters the subject's eye behaviour, which is captured in the raw data obtained by the eye tracker. Processing of raw eye tracking data may be carried out locally on the device or remotely, e.g., on a server, and may include preprocessing (e.g., filtering, removing outliers, etc.). Processing includes extracting data corresponding to selected features, and analyzing the data for the selected features. Features and analytic methods are described in detail in Examples 1, 2, 3, and 4 presented below, although they are not limited thereto.

Figures 2, 3:
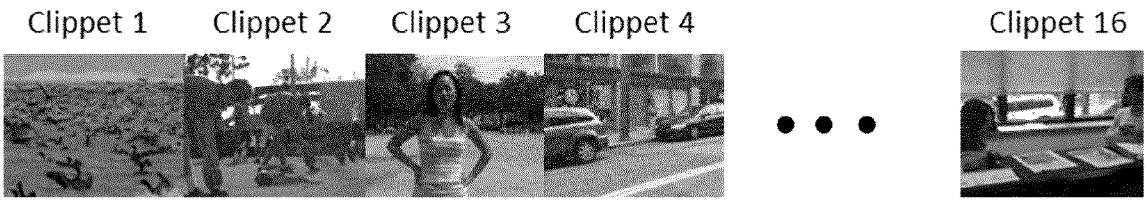
FIG. 2 is a flow diagram showing steps for processing eye tracker data to extract and classify features for detecting, diagnosing, and/or assessing a brain disorder in a subject, according to a generalized embodiment.
FIG. 3 is a diagram showing an example of a movie prepared from a sequence of short clippet movie sequences for an unstructured viewing task, according to one embodiment.

For example, as shown in FIG. 1A at 110, selected features may include saccade, blink, and pupil behaviour. FIG. 2 is a data processing flow or "pipeline" according to an embodiment wherein extracted features include saccade reaction time (SRT), microsaccades, blinks, and pupil behaviour. Other features may be extracted, as described in detail in Examples 1, 2, 3, and 4, below. As shown in FIG. 1A at 120, further processing may include, e.g., the processor analyzing data for each of the selected features using a classifier to determine a condition, validating the classifier for the determined condition(s) through comparisons to meta-data and the true condition if available, and generating an output based on the determined condition(s) for the selected features. Meta-analysis may be based on one or more of demographic information, vitals, medical examination, and established medical tests for a condition. Vitals may include, but are not limited to, blood pressure (both sitting and standing), pulse rate (both sitting and standing), respiration rate, waste and hip ratios. Validating may be performed for developing (i.e., training) the classifier. Once the classifier is trained and validation has been completed, validation may no longer be used. Accordingly, in embodiments used for evaluating and diagnosing subjects, the classifier may be already trained and the classifier output may be directed to storage in a database, e.g., in a server, in the cloud, etc. and used to determine an output such as a patient report; consequently the step of validating through comparisons to meta-data may be omitted, e.g., as shown in FIG. 1B. Embodiments may be based on machine learning, for example, using artificial intelligence techniques such as deep learning, a decision tree, or a support vector machine (SVM).

In further analyses, subtypes of brain disorders may be detected, demonstrating the sensitivity to the degree of cognitive impairment in the disorder that may be achieved by embodiments. For example, Example 3 describes subgroups detected for Parkinson's Disease (PD). Example 4 describes the detection of four PD related conditions. Similar results have been obtained for Alzheimer's Disease (AD). Oculomotor biomarkers (i.e., features) have been found and used to diagnose various neurodegenerative disorders as described herein; see, e.g., Examples 1 to 5 and FIGS. 13, 15, 16, and 17.

Finally, referring again to FIG. 1A, an output 130 may be provided to the subject and/or a medical professional indicating the likelihood of the subject having a brain disorder, and optionally other information such as the degree or severity of impairment.

As used herein, the term "saccade" refers to rapid conjugated eye movements that shift the center of gaze from one part of the visual scene to another. Saccades may include macrosaccades, which refers to gaze displacements of 2 degrees or more of visual angle, or microsaccades, which refers to gaze displacements of less than 2 degrees of visual angle.

As used herein, the term "smooth pursuit" refers to smooth conjugated eye movement that maintains a moving visual object in the center of gaze.

As used herein, the term "visual scene" refers to a scene presented to a subject on a display. The visual scene may include content associated with structured viewing tasks or unstructured viewing tasks.

As used herein, the term "structured viewing task" refers to an active viewing task wherein a subject is instructed to perform a task based on stimuli presented. Stimuli may be presented in the visual scene. In some embodiments, stimuli may also include one or more other modalities, such as auditory stimuli or tactile stimuli. For example, a structured viewing task may require the subject to look toward a stimulus in the visual scene (i.e., a "pro-saccade" task), or may require the subject to look away from a stimulus in the visual scene (i.e., an "anti-saccade" task). In some embodiments a structured viewing task may include both pro-saccade and anti-saccade tasks. An example of such a structured viewing task is presented in Example 3. In other embodiments, structured viewing tasks may be based on predictive (Calancie et al. 2022) or memory based models, smooth pursuit models, fixation tasks, reading tasks (Al Dahhan et al. 2017; 2020), etc. In some embodiments, the task may require the subject to perform actions using other modalities, such as manually pressing a button or interacting with a touchscreen.

As used herein, the term "unstructured viewing task" or simply "unstructured viewing" or "free viewing" refers to a passive viewing task wherein a subject is instructed to simply watch or observe a visual scene, without any other guidance or specific instruction provided (Tseng et al. 2013, Habibi et al. 2022). For example, in an unstructured viewing task the visual scene may be a video clip, or a series of video clips (also referred to herein as "clippets") presented one clip after another. The video clips may be prepared from any available content (e.g., video available online, movies, etc.) or custom made. An example of such an unstructured viewing task is presented in Example 1.

In accordance with embodiments described herein, an unstructured viewing task may include a visual scene based on a series of movie/video clips wherein the content of the clips is selected having regard to the nature of the brain disorder being investigated. Further, content that is expected to cause the subject to switch brain pathways upon viewing may be selected in order to elicit a detectable response from the subject. For example, subjects with eating disorders may be presented with content relating to food; subjects with dyslexia may be presented with content relating to reading or visually and phonetically confusing combinations of letters, symbols, and objects; subjects with emotional disorders may be presented with content relating to faces displaying emotions or other emotion-related content, etc.

IMPLEMENTATION

Embodiments may be implemented at least partially in computer code executable by a computing device (e.g., a smart phone, tablet, laptop computer, desk top computer, server, etc.), or network of computing devices, referred to generally herein as a computer. Such computer may include a non-transitory computer-readable storage medium, i.e., a storage device or computer system memory (for example, one or more magnetic storage disks, one or more optical disks, one or more USB flash drives), etc., having stored thereon the computer code. The computer code may include computer-executable instructions, i.e., a software program, an application ("app"), etc. that may be accessed by a controller, a microcontroller, a microprocessor, etc., generally referred to herein as a processor of the computer. Accessing the computer-readable medium may include the processor retrieving and/or executing the computer-executable instructions encoded on the medium, which may include the processor running the app on the computing device.

Executing the stored instructions may enable the computer to carry out processing steps in accordance with embodiments described herein, for example, processing steps for implementing one or more features such as a user interface, structured and/or unstructured viewing tasks, data preprocessing and processing pipelines, data analysis and classification, and outputting a patient report, as described with respect to the embodiments of FIGS. 1A, 1B, and 2. Some processing steps may include prompting a user for input. In some embodiments the programmed media may include stored video clips for use with viewing tasks. In some embodiments the computer code may be executed such that features of the embodiment of FIGS. 1A and 1B are implemented on the same computer, e.g., on a local computer in a clinical setting where the subject performs structured and/or unstructured viewing tasks and data processing, analysis, and output of a patient report are all performed locally. In other embodiments, features of the embodiment of FIGS. 1A and 1B may be implemented remotely (e.g., on a server) with the subject's computer connected (e.g., over a wired or wireless network, the internet, etc.) to the remote computer or server such that at least some features are implemented on the subject's computer. Some embodiments may require the subject to log in to the remote computer or server in order to perform structured and/or unstructured viewing tasks.

Thus, also provided herein is programmed media for use with a processor, wherein the programmed media includes computer code stored on non-transitory computer readable storage media compatible with the computer, the computer code containing instructions to direct the processor to carry out processing steps in accordance with embodiments described herein, for example, processing steps corresponding to features described with respect to FIGS. 1A, 1B, and 2.

Embodiments are further described by way of the following non-limiting examples.

Example 1

This example relates to an eye tracking classifier based on machine learning, with a support-vector-machine (SVM) as the core model. The methods are described as applied to eye tracker data obtained from subjects performing an unstructured viewing task. However, it will be appreciated that the methods can also be applied to eye tracker data obtained from subjects performing a structured viewing task.

Unstructured Viewing Task 140 subjects with early Parkinson's Disease completed the task as part of the Ontario Neurodegenerative Disease Research Initiative (ONDRI; https://ondri.ca/) at clinics across Ontario, Canada. 128 of these subjects (98 Male, mean age 67.8+/−6.6 years) were able to complete the eye tracking platform. Data for 98 age-matched controls (35 Male, mean age 67.7+/−8.1 years) were collected under identical conditions at Queen's University, Kingston, Ontario, Canada.

Each subject's eyes were tracked using a SR Research Eyelink 1000 Plus eye tracker (SR Research Ltd., Mississauga, Ontario). One eye (right) was tracked at 500 Hz sample rate. The subjects rested their head in a chin and forehead rest to allow for head stability. A Viewsonic VG732M 17" screen was attached to an articulating arm. This arm also held the camera and infrared illuminator of the eye tracker. This ensured that camera and monitor relative positions could be held constant and for ease of use in the clinic.

For the task, a Dell Latitude E7440 Laptop was used to deploy a free viewing task. The task consisted of 10, 1-minute high definition movies (i.e., video clips), played back at 30 fps and a resolution of 1280×1024 pixels (see, e.g., FIG. 3). Before the beginning of the task, the right eye was calibrated using a 9-point, regularly spaced grid on the monitor on a black background. The eye was calibrated to an average visual angle error of 0.57+/−0.21 degrees. Each movie was made in house and consisted of 16 or 17 clippets (short sub-movies) of approximately 2-4 s in length. Therefore, the movie appears to the participant as if the channel is being changed every few seconds as they watch, which encourages the subject to continually redeploy their attention to new scenery. Scenes were varied in content, generally pleasant in nature, and included natural scenes, cartoon, animals, humans in various interaction, etc. Subjects were only instructed to "watch the movies and pay attention". No other guidance or instruction was required.

Extraction of Features and Analyses

Raw eye tracking data (x-position, y-position, pupil-area) were extracted and processed using a custom software pipeline in Matlab (The Mathworks, Inc., Natick, Massachusetts). Data processing included detecting rapid eye movements (macrosaccades and microsaccades, for example), smooth eye movements (smooth pursuit), fixations, pupil dynamics, and blinks.

The core of this model is the extraction of explanatory features from the unstructured free viewing data. Categories of features were selected to cover the continuum of brain areas spanning the bottom-up and top-down eye movement circuitry of the brain. At total of 58 features are described below.

Features included basic oculomotor measures of eye movement, blinks, and pupil dynamics (i.e., behaviour), as listed in Table 1.

TABLE 1

| Oculomotor Features | | |
|---|---|---|
| Feature | Description | Measure |
| Baseline Pupil | Average pupil size in arbitrary units from the eye tracker | Mean |
| Saccade Duration | Time from onset to offset of saccade (ms) | Mean |
| Saccade Peak Velocity | Maximum velocity during a saccade (deg/s) | Mean |
| Saccade Amplitude | Linear distance of saccade from start to end point | Mean |
| Fixation Duration | The time between 2 successive saccades (ms) | Mean |
| Number of Blinks | | Number |
| Number of Saccades | | Number |
| Distance of gaze from center of screen | The size of the absolute difference in visual angle between all eye movements and the center of the screen (deg) | Mean |
| Saccade velocity threshold | 2 standard deviations above fixation velocity of eyes | Mean |

Figures 4A, 4B, 4C, 4D:
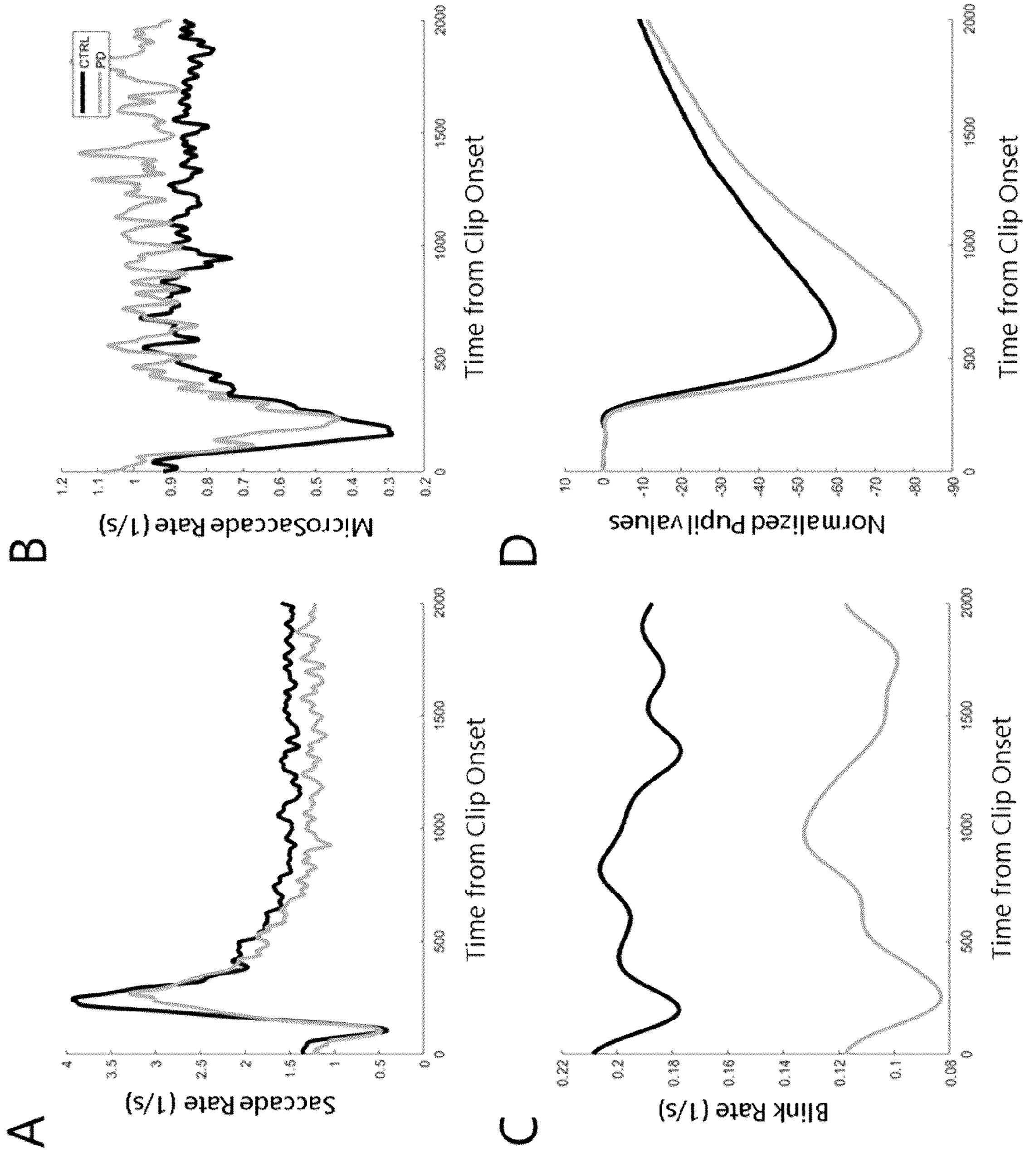
FIGS. 4A-4D are plots generated from an unstructured viewing task showing eye tracking dynamics relative to the start of clippets for Parkinson's (PD) in grey and control (CTRL) in black for saccade rate (A), microsaccade rate (B), blink rate (C), and pupil size (D).

Second, the data were processed into trials, which began at the onset of each clippet change and extended until the frame before next clippet started. At the clippet change, the visual input is abruptly changed with new scenery causing an abrupt visual perturbation in the brain. Early into this perturbation the brain employs more bottom up, automatic processing in response to low-level or basic visual properties of the scene (e.g., colors, motion, edges, contrast). As an example, aligning all data for each subject on all clippet changes throughout the 10 movies produces the plots of FIG. 4A-4D. As can be seen in FIG. 4A-4D, the dynamics of saccades (A), microsacades (B), blink rate (C), and pupil size (D) varies in a complex, functional manner throughout the clippets. However, definite structure can still be observed, such as a saccade inhibition and rebound in reference to the new scenery (FIG. 4A) and a pupillary light reflex with differing amounts of constriction (FIG. 4D).

Figure 5:
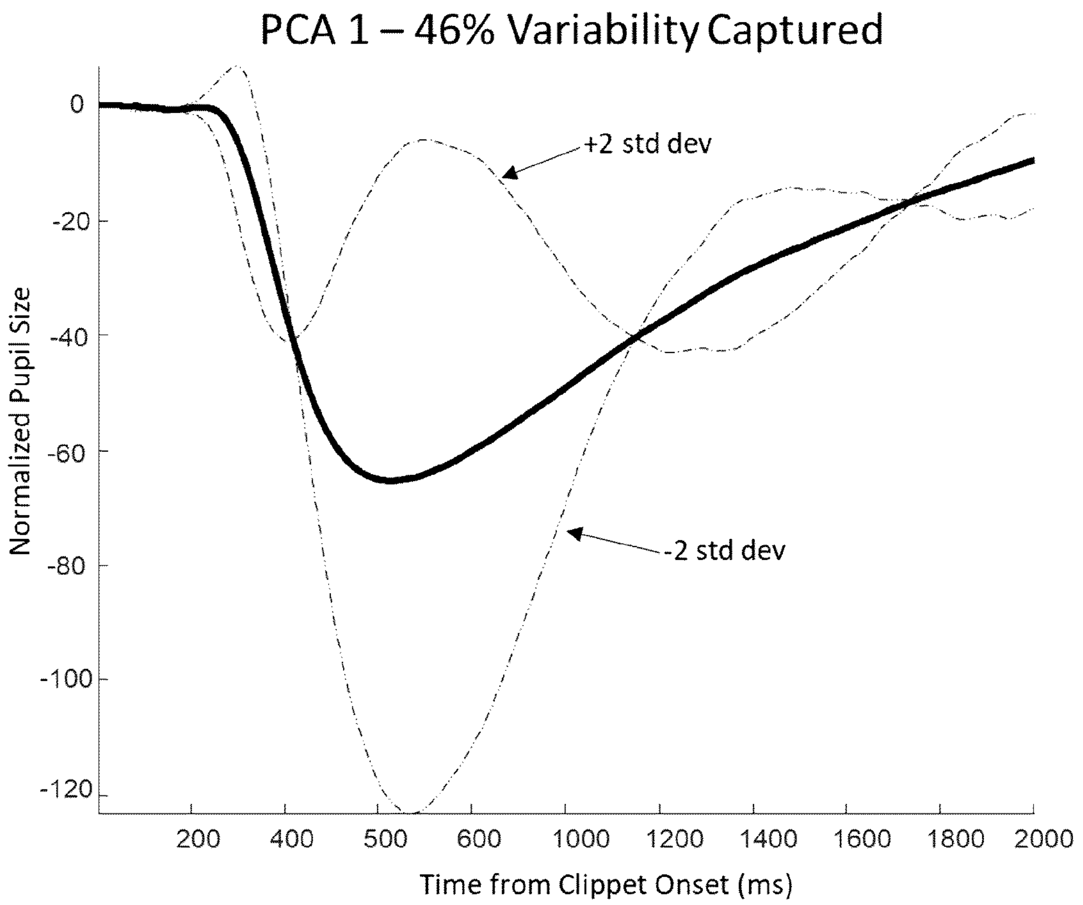
FIG. 5 is a plot showing results of a Functional Principal Components Analysis (FPCA) of pupil dynamics for data obtained for an unstructured viewing task, according to one embodiment.

The challenge with this data is that it is functional in nature. To extract features, Functional Data Analysis (FDA) (Ramsay and Silverman, 2002) was used to produce harmonic scores. FDA allows functions to be treated as traditional statistical variables and traditional statistical analysis can be performed on them. The approach was to use Functional Principal Components Analysis (FPCA) to extract four harmonic scores for each functional dynamic that describes approximately 95% of the variability in these features. As in traditional PCA, these four scores reduce the dimensionality in an orthogonal manner. A varimax function was applied to capture variability more evenly among the scores (see FIG. 5 as an example output). FPCA was applied to saccade rates, microsaccade rates, blink rates, and pupil dynamics for the first 2 seconds after each clippet change (See Table 2). In FIG. 5, PCA component 1 for the pupil dynamics of all control and PD individuals is shown. The heavy curve is the average pupil size. Curves for-2 standard deviations away from the average and +2 standard deviations away from the average using the FPCA harmonic are shown. The first harmonic clearly captures variability related to the constriction, but also some smaller related oscillations. Each subject was given a harmonic score relative to these functions.

TABLE 2

| Functional Data Analysis | | |
|---|---|---|
| Feature | Description | Measure |
| Blink Rate Harmonics | Blinks are defined by a loss of eye tracking in a predictable manner related to the closing and opening of the eyelid. We viewed this data as a rate of blinks/second. | Functional PCA |
| Saccade Rate Harmonics | Saccades are defined as the periods where the velocity of eye movements rise above fixation velocity and are ballistic in nature. We viewed this data as a rate of saccades/second. | Functional PCA |
| Microsaccade Rate Harmonics | Microsaccades are defined exactly as saccades but are restricted to those with amplitude of less than 2 degrees of visual angle. These are more related to fixational stability and are viewed as a rate of microsaccades/second. | Functional PCA |
| Pupil Harmonics | Raw pupil data has arbitrary units, but relative changes are meaningful. Therefore, we normalized Pupil size to the beginning of each clip and viewed the dynamics of change. | Functional PCA |

Figure 6:
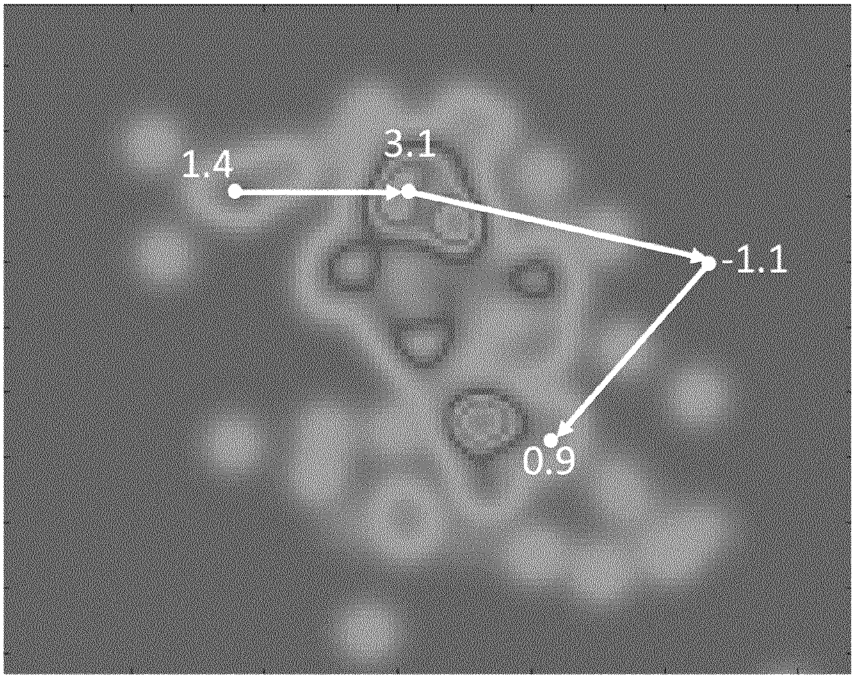
FIG. 6 is a group-level gaze map of controls for one frame of one movie for an unstructured viewing task, with a theoretical individual scan path overlayed, according to one embodiment.

The third set of features were related to the correlation of gaze for subjects relative to each other and relative to the contents of the scene. The correlation of gaze, regardless of comparison, was computed as the correspondence of a subject's fixations with some heat map. This is measured use Normalized Scanpath Saliency (NSS) (Peters et. al., 2005). The object is to generate a normalized map (subtract the mean and divide by the standard deviation) over each frame of the movie, relative to some interesting property. Then sample the value of this map at each fixation point for a subject (allowing for a small amount of error comparable to the error in calibration). The average of these values indicates how many standard deviations above or below the mean of the map a subject's gaze is. The higher this value, the more correlated a subject's gaze is with a particular map. FIG. 6 is a group-level gaze map of controls for one frame of one movie, with a theoretical individual scan path overlayed. Group gaze positions are represented as Gaussian blobs and summed on the group level. The brighter areas indicate where gaze correlated between the subjects. As can be seen, this individual scan path produced four fixations with various NSS values throughout the frame. This process may be run for every frame for every movie for each individual to get average NSS scores.

Gaze was compared in two types of maps. The first maps were inter-observer maps and represent the gold standard for gaze. These are constructed by averaging the gaze of all control subjects for every frame into a heat map. A subject's gaze is represented as a small 1.5 degree Gaussian patch to allow for some error. These individual gaze maps are then summed and normalized to generate group gaze maps (see FIG. 6, background). Each control subject was compared to a group map that they were left out of. This map measures both bottom-up and top-down processing. In particular, this gold-standard map captures the volitional movements of the group. Considering the control group as normative behaviour, NSS scores capture the intactness of volitional processing.

Figure 7:
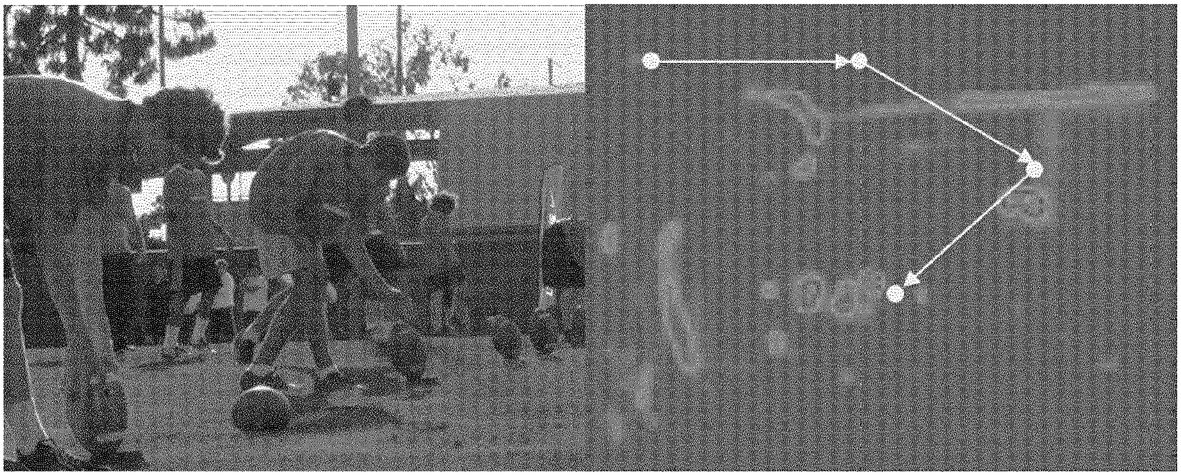
FIG. 7 shows an example of a saliency map (right) and the frame of a movie clippet on which it is based (left) for an unstructured viewing task, according to one embodiment.

Bottom-up saliency maps of various forms were also generated. These maps have been shown to strongly predict the first few saccades a participant makes in response to a novel stimuli, such as a new clippet (Itti, et. al., 2001). These saccades are largely automatic and in response to basic features of a scene such as motion, intensity, and colour). FIG. 7 is an example of a saliency map (right) and the frame it is based on (left). Although not shown in colour, this map represents red/green colour saliency. Thus, NSS scores in relation to these maps capture the intactness of these automatic processes. These maps were generated using automated tools from the laboratory of Laurent Itti (iLab Neuromorphic Vision C++ Toolkit, http://ilab.usc.edu/toolkit/). Table 3 provides a list of maps that were compared.

TABLE 3

Saliency/Gaze Map Comparisons

| Feature | Description | Measure |
| --- | --- | --- |
| Inter-observer NSS | Comparison to control gold standard | Mean |
| Human face NSS | Comparison to a map of faces. Faces were modelled as a Guassian blob with width and height relative to the width and height of the face in the frame. Faces were outlined manually and automatically. | Mean |
| Saliency - Motion NSS | Itti model of motion | Mean |
| Saliency - Flicker NSS | Itti model of flicker | Mean |
| Saliency - Intensity NSS | Itti model of intensity (luminance) | Mean |
| Saliency - Red/Green Colour NSS | Itti model of the red/green channel | Mean |
| Saliency Blue/Yellow Colour NSS | Itti model of the blue/yellow channel | Mean |

A further set of features was based on the raw x-position, y-position, and pupil area data. It was observed that the structure of the raw data alone was descriptive and may capture some variability between the groups missed in the hand-crafted features. Traditional statistical measures 5 of these data were examined as outlined in Table 4.

TABLE 4

Raw Data

| Feature | Description | Measure |
| --- | --- | --- |
| Raw X/Y/Z mean | | Mean |
| Raw X/Y/Z standard deviation | | Standard Deviation |
| Raw X/Y/Z kurtosis | Kurtosis measures how weighted the tails of a distribution are with outliers | Kurtosis |
| Raw X/Y/Z skew | Skewness measures how evenly the data is distributed around the mean | Skew |
| Raw X/Y/Z entropy | The Shannon Spectral Entropy of the data. This measures the structure in the data. The higher the entropy, the more random the data is. | Entropy |

Classifier Model

In this example the classifier model was built on a Support Vector Machine (SVM). The SVM assigned data as belonging to a category such that the distance between different categories (the margin) was maximized.

To build the model, all 58 features as described above were used. The data were first cleaned, resulting in the exclusion of some subjects. For controls, a robust and objective outlier detection algorithm (Filzmoser, et. al., 2008) that works on high dimensional data via principal components analysis was applied. Justification for the outlier detection was that it was assumed a subset of controls were not actually controls. By sampling from the community, some of the elderly participants were likely prodromal for PD or other cognitive degeneration. Because the eye tracking measures are sensitive to these disorders, the aim was to objectively remove a subset of the subjects that were outliers.

In addition, for the control (CTRL) and PD groups, any subjects who did not complete at least five movies with good quality eye tracking (i.e., they were paying attention and tracked) or if they had poor calibration (greater than 2 degree average error) were removed. In total, the clean data consisted of 117 PD subjects and 76 CTRL subjects.

Figure 8:
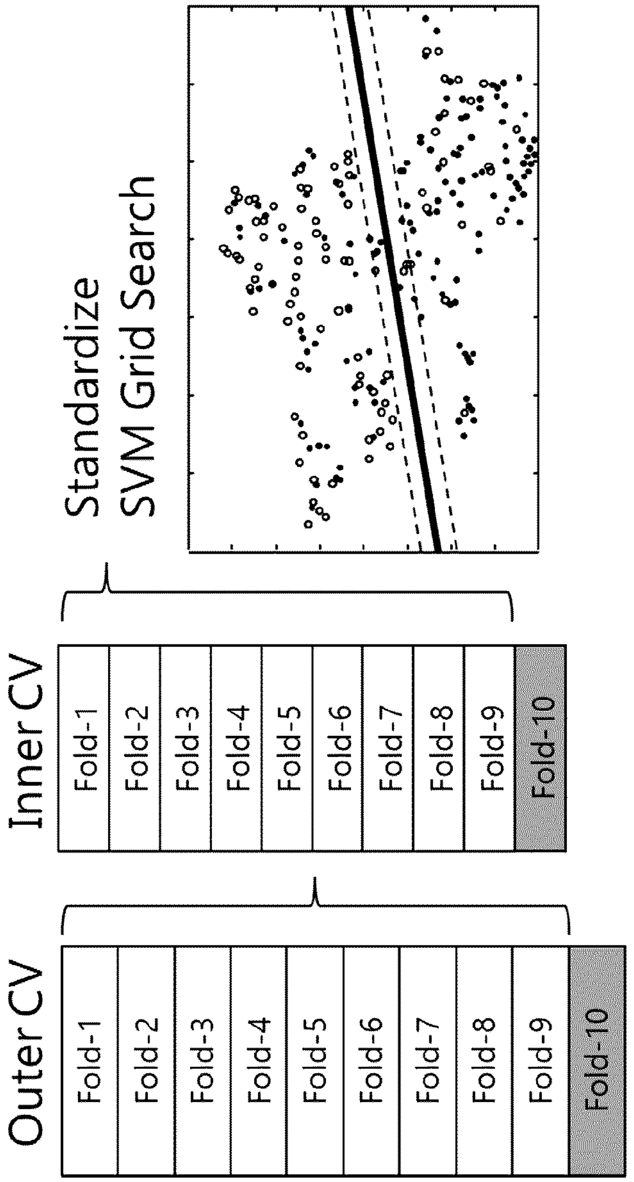
FIG. 8 is a diagram showing a model-building process using a Support Vector Machine (SVM), according to one embodiment.

To test the model, a nested cross validation (CV) scheme was employed to avoid data leakage and to predict real-world performance more accurately (see FIG. 8). All models were built in Python using the sklearn package. In the outer CV, one test set of data is held out and the other folds are used to train and validate the model. In the inner CV, the data are standardized and a grid search of the SVM regularization parameters is performed for the best fit to the training data. Note that the SVM used a radial basis function and was weighted relative to the asymmetry in group numbers to avoid bias. After 10-folds of iteration average accuracy measures were obtained for the binary classification.

Preliminary Results

Figure 9:
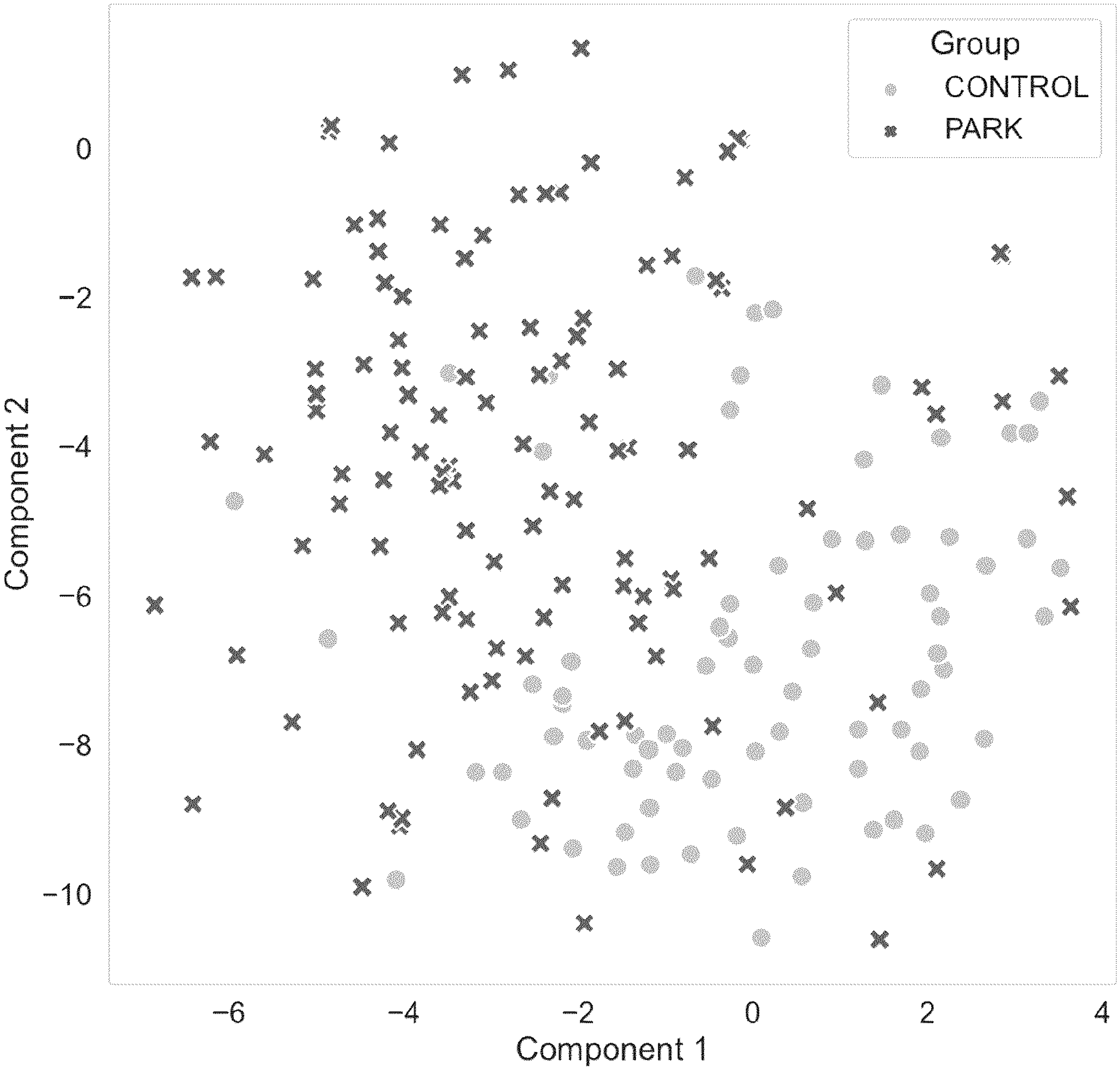
FIG. 9 is a plot showing a t-distributed Stochastic Neighbor Embedding (tSNE) dimensionality reduction of raw data from an unstructured viewing task, according to one embodiment.

Qualitatively, the features were analyzed using t-distributed Stochastic Neighbor Embedding (tSNE) dimensionality reduction (van der Maaten, et. al. 2008) and the results were plotted in 2D (FIG. 9), where a clear separation between the groups can be seen. The extracted features appear to provide a good separation between the groups and are well suited for a traditional classifier such as SVM.

Figure 10:
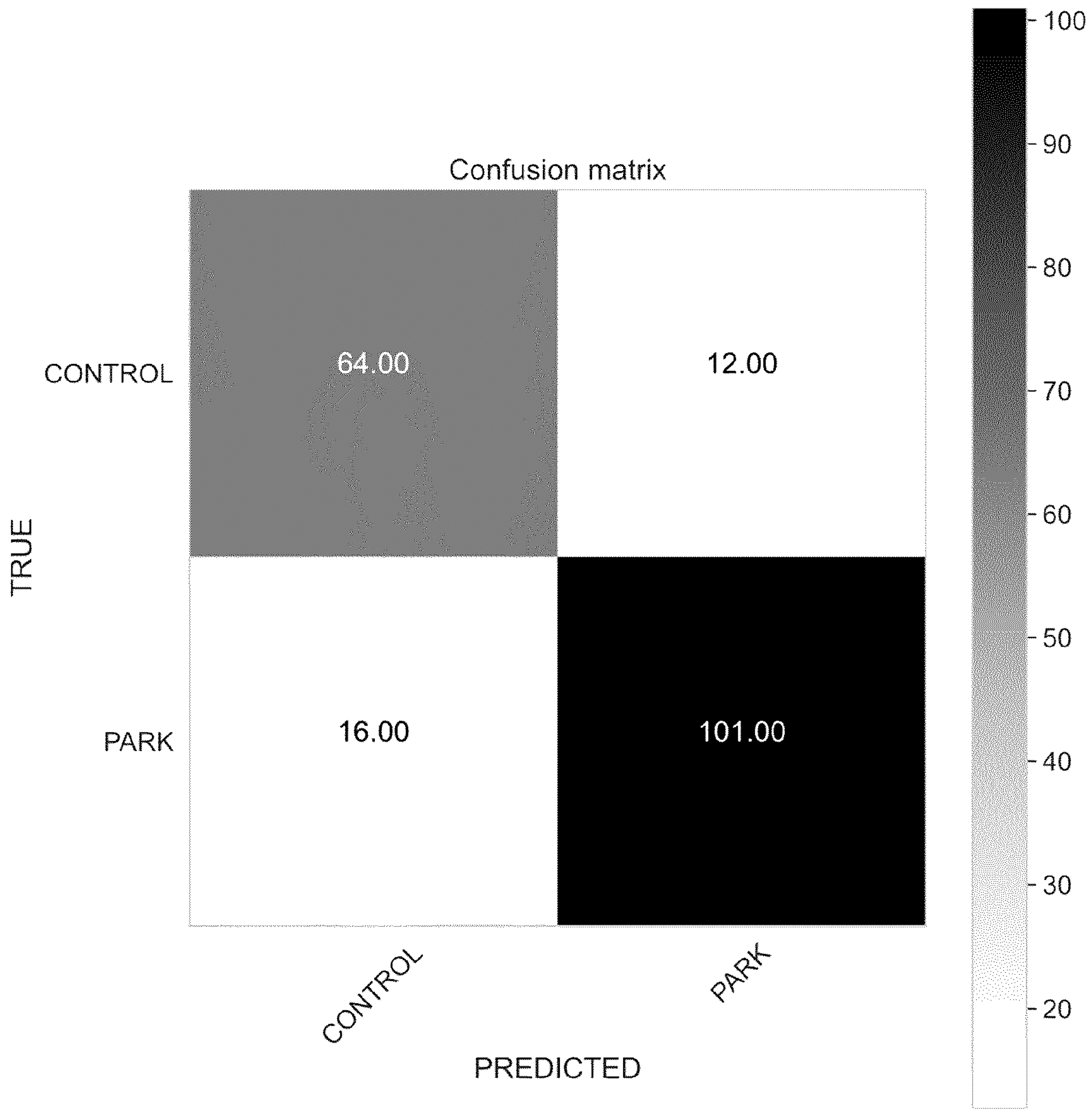
FIG. 10 is a confusion matrix based on data from an unstructured viewing task, according to one embodiment.
Figure 11:
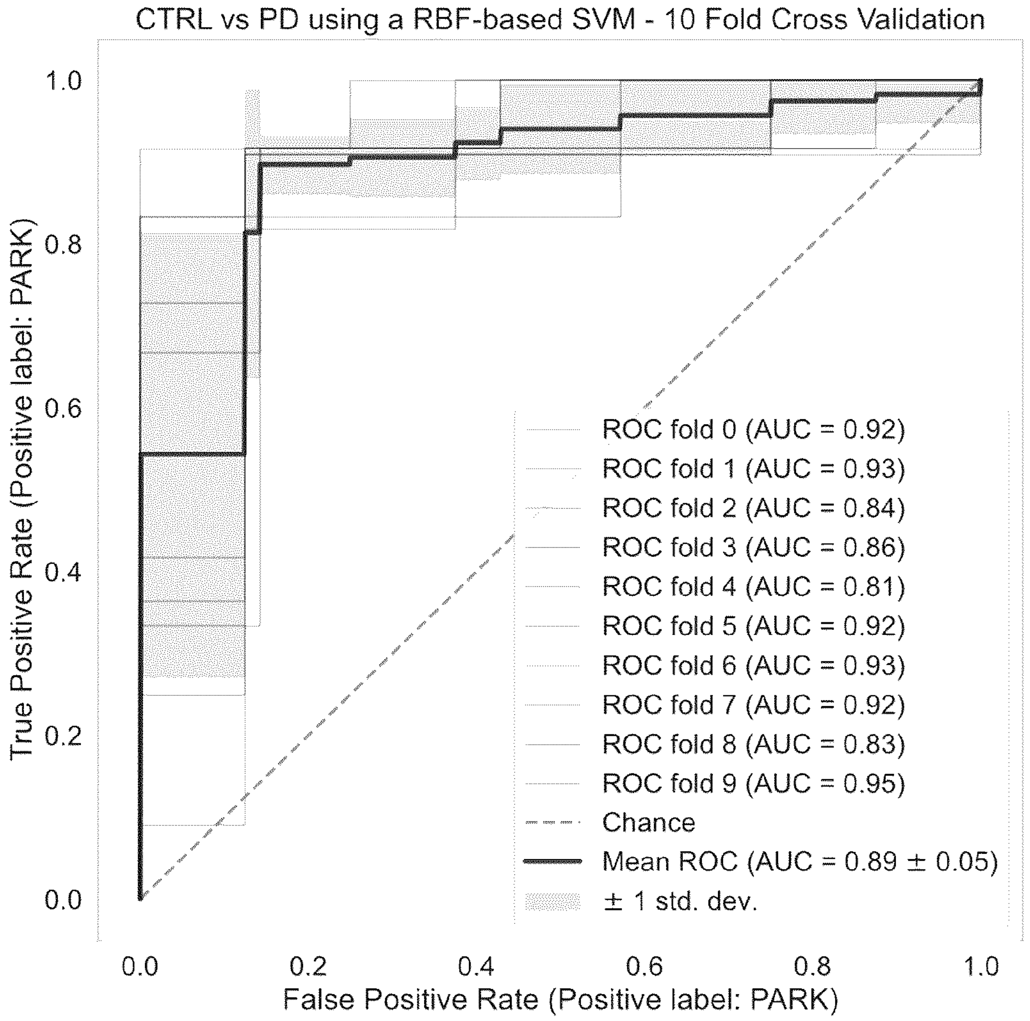
FIG. 11 is a ROC analysis of 10-folds data, where the ROC for each fold is shown in light thin lines, with the average shown in the solid heavy line and standard deviation around the mean is shown in shading, based on data from an unstructured viewing task, according to one embodiment.

By predicting a class for each subject in each test set, an approximate confusion matrix can be constructed as shown in FIG. 10. An overall accuracy of 84.5%, with a sensitivity of 87% and a specificity of 80% are achieved. Further, an ROC analysis of 10-folds (FIG. 11) shows an average AUC value of 89%+/−0.1% (Note that results vary slightly with every run due to randomness in the CV). In FIG. 11, the ROC for each fold is shown in light thin lines, with the average shown in the solid heavy line. Standard deviation around the mean is shown in the shaded area.

Figure 12:
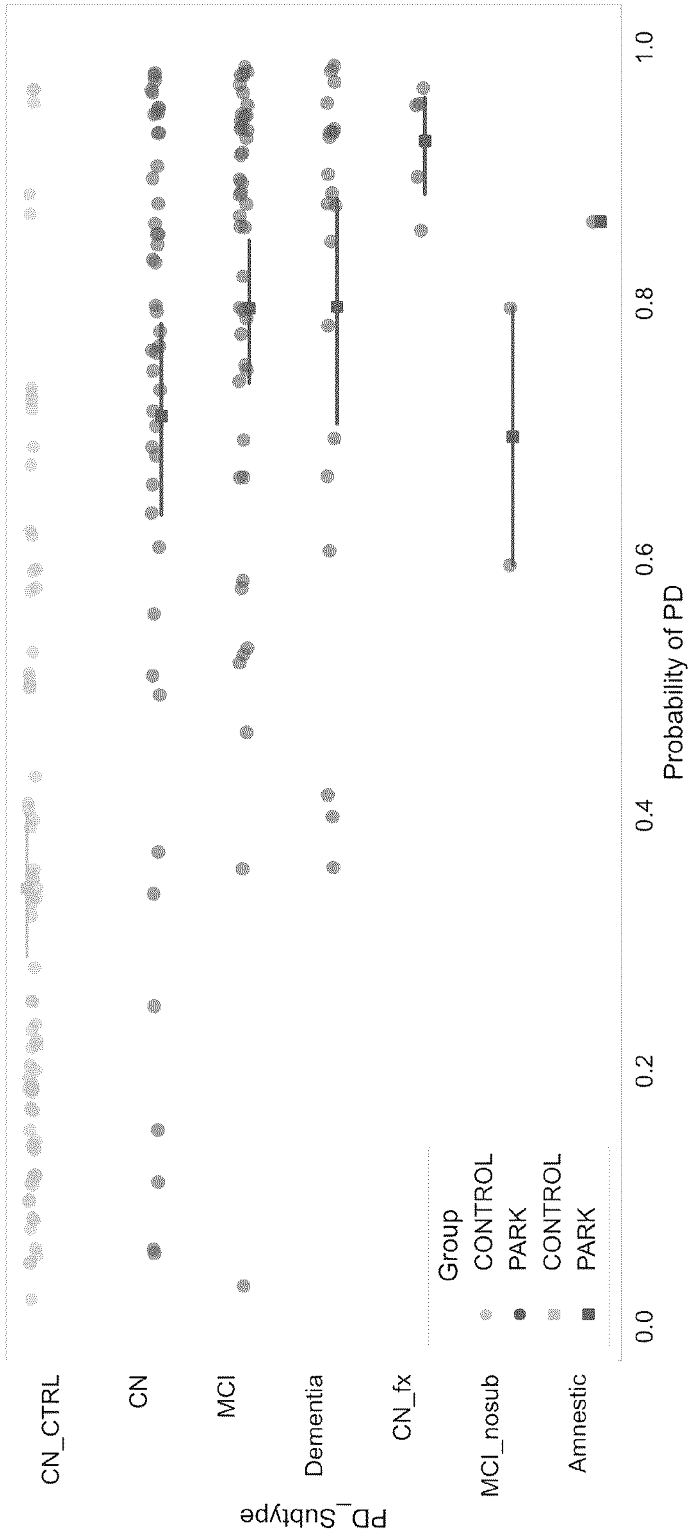
FIG. 12 is a plot showing probability of Parkinson's Disease (PD) in MDS subgroups, based on data from an unstructured viewing task according to one embodiment, wherein increasing confidence in PD can be seen in more cognitively impaired subgroups; means+/−standard error are displayed as small black boxes with lines, CN_CTRL=controls.

Finally, to investigate the false negatives (and false positives) and understand more about the sensitivity of eye tracking measures to disease progression, the predicted probability of PD from the SVM was plotted with their MDS Cognitive Classification (provided by the ONDRI study). The criteria for sub-classification on the MDS scale are shown in Table 5. FIG. 12 shows probability of PD, as assigned by this classifier for controls and subgroups of PD, wherein means+/−standard error are displayed as small black boxes with lines. The top row represents controls (CN_CTRL), followed by cognitively normal (CN) PD, although there are false negatives. The next row is PD+mild cognitive impairment (MCI), followed by PD+dementia subtypes. As can be seen, there is increasing confidence in PD assigned to groups with more cognitive decline, with the general trend of fewer false negatives and a higher confidence in the prediction moving down the plot. A 1-tailed t-test of CN PD vs all other PD groups shows a significant difference in probability ($p=0.032$). Therefore, the classifier is not only sensitive to PD but measures the level of cognitive decline. Also, the most false negatives are in the CN PD group. Interestingly, a subset of controls groups is predicted with PD as false positives, with some almost 100% confident in PD, indicating the possibility of some form of cognitive decline that may be undiagnosed.

TABLE 5

| MDS Classification Criteria (iADLs = Instrumental Activities of Daily Living) | |
|---|---|
| Shortcut | Description |
| CN | Cognitively normal no assistance in iADLs |
| CN_fx | Cognitively normal with assistance in iADLs |
| MCI | Cognitive impairment with subjective decline and no or minimum assistance in iADLs |
| MCI_nosub | Cognitive impairment with no or minimum assistance in iADLs but no subjective decline |
| Amnestic | Isolated memory impairment with subjective decline and moderate to significant assistance in iADLs |
| Dementia | Cognitive impairment with subjective decline and moderate to significant assistance in iADLs |

Example 2

This example describes features of eye behaviour that may be extracted from raw eye tracker data (see also Examples 4 and 5). The features may be grouped according to categories including saccade, blink, and pupil behaviour (i.e., features such as pupil constriction and dilation, other pupil responses). The features are described as applied to data obtained for an unstructured viewing task; however, it will be appreciated that the features are also applicable to data obtained for a structured viewing task. Extracted features A-Q are defined as follows, with reference to FIG. 13.

Figure 13:
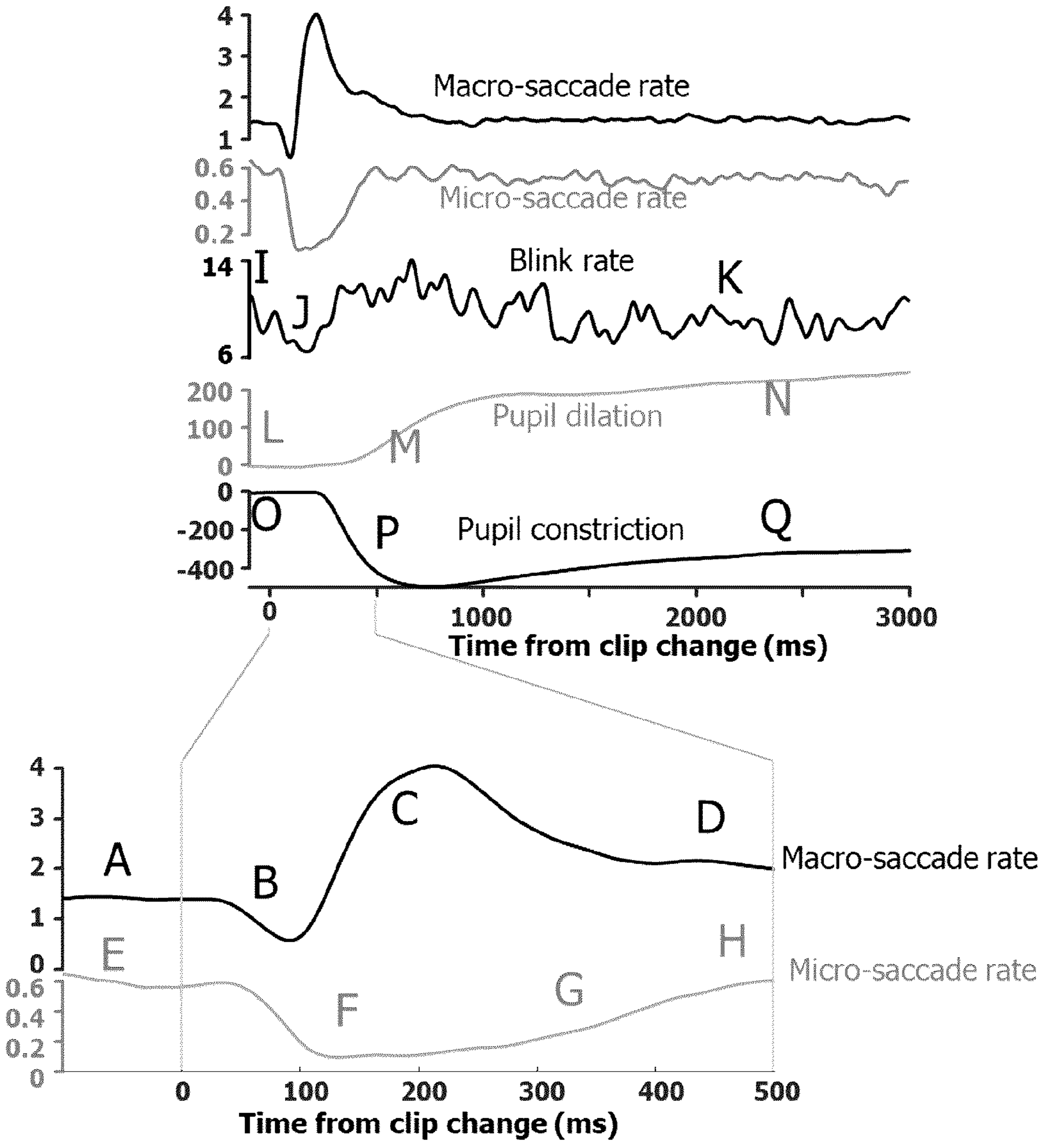
FIG. 13 is a diagram showing features of eye behaviour that may be extracted from raw eye tracker data, according to one embodiment.

Features A-D. Measures of macrosaccades. Macrosaccades are defined as all saccades > or =2 degree amplitude and the macrosaccade rate is computed by first counting the timing of each subject's saccades relative to a scene (e.g., clip) change and then averaging across subjects (FIG. 13).

A. Steady state saccade rate at the moment of clip change. The steady state rate varies across age and in many neurological diseases.

B. Saccade Inhibition. Starts about 60 ms after clip change and reaches a minimum at 90-100 ms in healthy young adults, slightly later in elderly. The timing and depth of the inhibition may vary in different neurological conditions.

C. Saccade rebound burst. Starts at about 100 ms in healthy young adults and up to 20-30 ms later in elderly. The saccade rebound burst is made of two independent components: C1 from 100-150 ms after clip change and C2 from 150-250 ms after clip change. The timing and magnitude of C1 and C2 may be altered in neurological disease.

D. Steady state saccade rate from 1000-3000 ms after clip change (similar to epoch A). The steady state rate is altered in many neurological diseases.

Features E-H. Measures of microsaccades. Microsaccades are defined as all saccades <2 degree amplitude and the microsaccade rate is computed by first counting the timing of each subject's saccades relative to scene (e.g., clip) change and then averaging across subjects (FIG. 13).

E. Steady state microsaccade rate at the time of clip change

F. Inhibition of microsaccades that begins ~60 ms after clip change. This inhibition is varied in different neurological diseases.

G. Slow rebound of microsaccade rate. This slow rebound varies in different diseases.

H. Steady state rate of microsaccades from 1000-3000 ms after clip change (similar to epoch E). The steady state rate may be altered in many neurological diseases.

Features I-K. Measures of blink rate. Compute blink rate by first counting the timing of each subject's eye blinks relative to scene (i.e., clip) change and then average across subjects (FIG. 13).

I. Steady state blink rate at the time of clip change.

J. Transient Inhibition in blink rate ~100-200 ms after clip change. Timing and depth of inhibition is reciprocally related to the saccade rebound burst and varies greatly in neurological diseases.

K. Steady state blink rate from 1000-3000 ms (similar to epoch I).

Features L-N. Pupil dilation response. Isolate scene (e.g., clip) transitions (e.g., 20% of transitions) with biggest luminance decrease and then average each subject's pupil response for this subset of clip changes to isolate and optimize pupil dilation responses.

L. Pupil size at end of previous clippet.

M. Timing, magnitude, and speed of phasic dilation response.

N. Steady state dilation response.

Features O-Q. Pupil constriction response. Isolate scene (e.g., clip) transitions (e.g., 20% of transitions) with biggest luminance increase and then average each subject's pupil response for this subset of clip changes to isolate and optimize pupil constriction responses.

O. Pupil size at end of previous clippet.

P. Timing, magnitude, and speed of phasic constriction response.

Q. Steady state constriction response.

Additional Features Including:

Visual saliency response on the pupil. A small response on the pupil that is locked in time to the scene (e.g., clip) change and starts at about 130 ms. This small pupil response consists of a brief pulse of dilation, followed by constriction.

Saccade command on the pupil. A small response on the pupil that is time locked to saccades (occurring approximately 150 ms after the saccade). This saccade-aligned response scales with saccade amplitude.

Saccade-blink inhibition. Saccades and blinks are mostly exclusive and a central brain circuit ensures inhibition between saccade and blink behavior.

Example 3

This example describes features of eye behaviour that may be extracted from raw eye tracker data. The features are described as applied to data obtained for a structured viewing task; however, it will be appreciated that the features are also applicable to data obtained for an unstructured viewing task.

Structured Viewing Task

Subjects were seated in a dark room with their heads resting comfortably in a head rest and their eyes were approx. 60 cm away from a 17-inch 1280×1024 pixel resolution computer screen. An infrared video-based eye tracker (Eyelink 1000 Plus, SR Research Ltd, Ottawa, ON, Canada) was used to track monocular eye position at a sampling rate of 500 Hz.

Basic demographic information about each subject was digitally collected using a custom software program that performed error checking on naming conventions, launched the task automatically, and then saved the data and the demographic information in a common folder to reduce errors in data collection.

Figure 14:
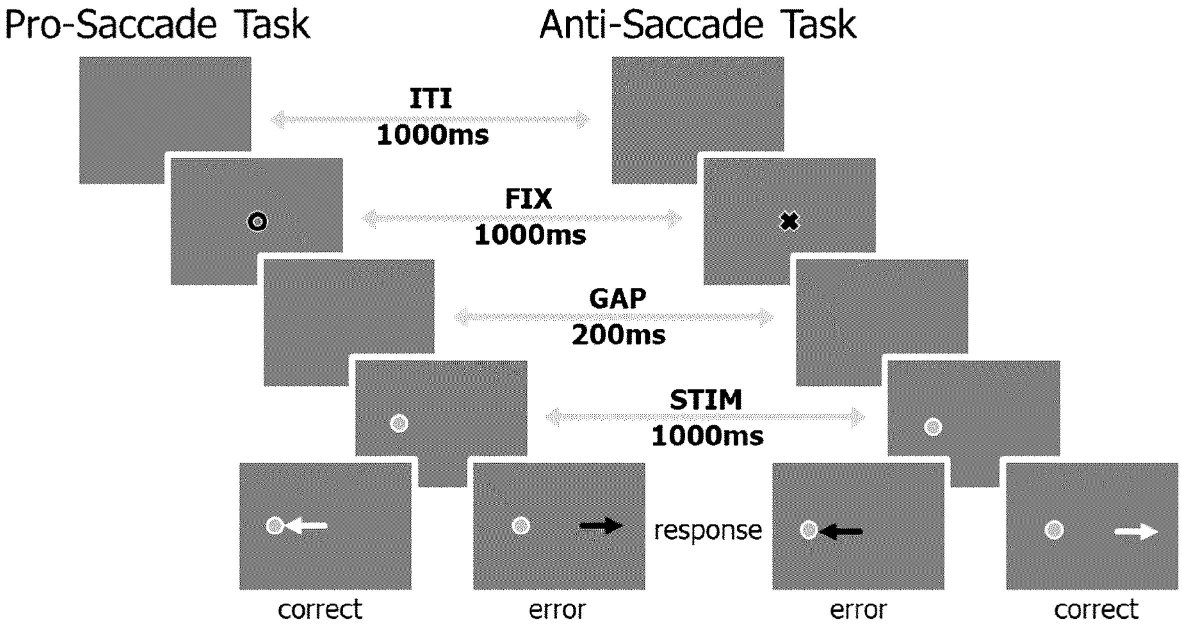
FIG. 14 is a diagram showing a method for a structured viewing task according to one embodiment based on interleaved pro-saccade and anti-saccade tasks.

The task (see FIG. 14), referred to as IPAST (Interleaved Pro and Anti Saccade Task) consisted of two blocks of 120 trials, lasting approximately 20 minutes in total. FIG. 14 shows sequences of displays for a pro-saccade task (left side) and an anti-saccade task (right side). Each trial started with 1000 ms of an inter-trial interval ("ITI"), typically a blank black screen (0.1 cd/m$^2$), during which subjects are free to move their eyes and/or blink. This was followed by the appearance of a central fixation point (FP. 0.5° diameter, 42 cd/m$^2$) that lasted for 1000 ms on a black background (0.1 cd/m$^2$). The condition of each trial was revealed through the color of the central fixation point (green: pro-saccade, PRO; red: anti-saccade, ANTI). Following 1000 ms of fixation ("FIX"), the FP was removed from the screen, and the screen remained empty for 200 ms ("GAP" period). After the gap period, a peripheral stimulus (0.5° diameter dot; gray, 62 cd/m$^2$) appeared 10° horizontally to the left or right to the FP position ("STIM"). On PRO trials, subjects were instructed to make a saccade to the stimulus location as soon as it appeared ("correct", bottom left). On ANTI trials, subjects were instructed to not look toward the stimulus, and instead look toward the opposite direction from the stimulus ("correct", bottom right). If a subject failed to make the correct saccade (e.g., for ANTI, to suppress the drives that lead to a saccade toward the stimulus), this was called a Direction Error ("error"). The saccade conditions (PRO or ANTI) as well as stimulus locations (left or right) were pseudo-randomly interleaved with equal frequency. Special codes were logged in the EDF file to represent the timing of events and the nature of each trial.

In some situations, too few trials were collected to create a valid representation of the individual's behavior and abilities. Here, we employed a cut-off of at least 30 usable trials from both PRO and ANTI tasks per participant. This is equivalent to ¼ of the expected data count (i.e. 30/120 per task).

Data Pre-Processing

Data processing was completed using custom software In MATLAB (The Mathworks). Smoothing was performed using Matlab's filtfilt function (in a zero-phase manner) with a box shaped kernel for all filtering. This was the simplest form of smoothing because it treats all data points equally and has the fewest assumptions (e.g., a kernel of 3 would be [1 1 1]/3 and a kernel of 5 would be [1 1 1 1 1]/5. Thus, the larger the kernel, the wider the window, and the greater the smoothing).

Similarly, differential calculations for X and Y velocity were also done in. To calculate an instantaneous differential for a given point in time, the previous data point was subtracted from the following data point and then divided by 2. For the first and last data points, a simple 2-point difference was used.

$$vel_X = \frac{\left[X_2 - X_1, \frac{X_{3:n} - X_{1:n-2}}{2}, X_n - X_{n-1}\right]}{ds}$$

Where X is the vector of horizontal position (replace with Y for vertical data), n is the number of data points, and ds is the delta in seconds between each datapoint (ds=0.002 for 500 Hz recording). Eye speed in degrees per second was determined via the usual Euclidean process using both of the 3-point smoothed velocity vectors.

Blink Detection

Blinks generally have stereotypical durations and patterns on the pupil area data. In order to better isolate when data was lost two steps were taken to clarify the pupil area data. As the pupil area data (A) can be quite variable the first step was to normalize each trial to have the same average area.

$$A300 = \frac{A}{\text{mean}(A(A > 10))} * 300$$

The pupil area values ranged from the hundreds to the thousands. Thus, values below 10 were not included in the definition of the mean and the number 300 was arbitrarily chosen. This made the non-zero mean of the pupil area fixed to 300 (A300). The next step was to model the low-frequency modulation of A300 over time so it could be removed to create a flattened A300. The goal of this is to help clarify the sections of data that were indicative of eye loss. The next step was to create a smoothed velocity for the change in A300 (SVA), this was used to flag high velocity data for removal & replacement from the model of the low-frequency modulation. A 3-point kernel was used on the SVA to flag high velocity data for removal & replacement. A copy of the A300 data was created where the high velocity (SVA>1000) and small area (A300<2) data were replaced using linear interpolation between the preceding and following data points. Then the filled A300 copy was smoothed using a 50-point kernel to model the low-frequency modulation. This model was subtracted from the A300 to remove non-linear trends and create a flatter profile that exaggerates high velocity changes in area, which helped in detecting lost data. Once data loss was detected the area velocity (the change in area per measurement for the A300 data) was used to determine the start and end of the data loss. A smoothed absolute velocity was used with a dynamic threshold per trial. A 2-point derivative of area was calculated and smoothed with a 3-point kernel. The absolute value was taken and smoothed again creating a smoothed absolute velocity (SAV).

Saccade Detection

The detection of the onset of a saccade (given relatively good data) is a straightforward process of determining a speed threshold and then finding the first data point that is above it, with consecutive data points remaining above it for a given duration. The background noise during a known fixation epoch where eye speed was below a fixed threshold was used to determine the dynamic threshold for each trial. Thus, noisier trials had a higher threshold to avoid numerous false positives. 50 dps was used as the fixed threshold to find the mean and standard deviation of the background noise. The dynamic threshold for each trial was defined as the mean plus 2.5 times the standard deviation, but never less than 20 dps.

The end point of a saccade can be quite difficult to properly determine due to well-known aspects of video based recording. Video eye tracking uses the pupil to estimate gaze, and the pupil is defined by the everchanging iris. The iris not only expands and contracts, to change the diameter of the pupil, but due to fluid dynamics and rotational acceleration the orientation of the iris relative to the rest of the eye also changes, meaning that the pupil orientation does not always line-up with the orientation of the eye. According to this fluid-structure interaction the rotational acceleration and deceleration of the eye creates a slosh dynamics problem between two bodies of fluid with a flexible structure in between. Because the iris is flexible, the rotational acceleration of the eye and the inertia of the aqueous humor induces pressure strain on the solid structures of the eye that lie between the two liquid parts of the eye. Upon reaching a fixed (or zero) speed, this pressure is oscillatory and diminishes with each cycle until equilibrium is once again reached. Even healthy eyes have this motion and it interferes with proper detection of the end of a saccade. Thus, to accurately measure the endpoint of a saccade, one must wait for the oscillations to end. This artificially elongates the duration of saccade for individuals with greater humor-slosh. As a result, accuracy of the duration measurement is sacrificed for better accuracy of the end-point.

Figure 15:
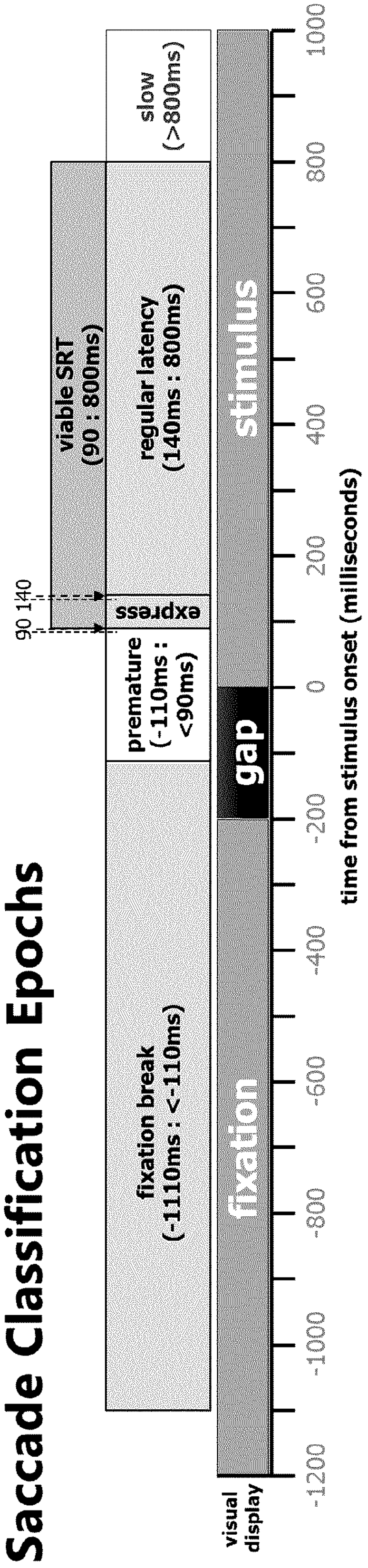
FIG. 15 is a diagram showing a saccade classification scheme for the structured viewing task of FIG. 14, according to one embodiment.

All detected saccades were classified as shown in FIG. 15 by when they occurred and their start and end points. For viable saccades Saccadic Reaction Time (SRT) was measured as the time between the appearance of the stimulus and the onset of the first subsequent saccade. Saccades to potential stimulus locations that happened prior to stimulus appearance and after fixation offset were termed ‘premature’ and were equally likely to be either correct or direction errors, indicative of a guessing behavior. In one embodiment, sensory impulses resulting from stimuli appearance cannot trigger saccades until approximately 90 ms after stimulus appearance; thus, the premature window is from −110 ms to 89 ms. Express and Regular latency saccades are separated and in this embodiment the two are delineated at 140 ms. Saccades that take place after 800 ms are extremely rare but do occasionally occur. These slow saccades are removed from measurements of latency and saccade metrics as they are outliers, and their effects weaken the representation of the individual’s behavior and abilities.

Example 4

This example describes an embodiment using eye tracking to identify and distinguish between Parkinson’s and related diseases (Habibi et al. 2022). This study 1) describes and compares saccade and pupil abnormalities in patients with manifest alpha-synucleinopathies (αSYN: Parkinson’s disease (PD), Multiple System Atrophy (MSA)) and a tauopathy (progressive supranuclear palsy (PSP)); 2) determines whether patients with rapid-eye-movement sleep behaviour disorder (RBD), a prodromal stage of αSYN, already have abnormal responses that may indicate a risk for developing PD or MSA. It is important to identify key differences in αSYN cohorts versus PSP which is a tauopathy. Early in the disease process, it is difficult to differentiate Parkinson’s-related diseases from PSP as they present with similar symptomatology. This example demonstrates that eye tracking and methods described herein provide a key component for proper diagnosis.

Ninety (46 RBD, 27 PD, 17 MSA) patients with an αSYN, 10 PSP patients, and 132 healthy age-matched controls (CTRL) were examined using 10 1-minute videos (15-17 clippets each)-based eye-tracking task (Free Viewing). Participants were free to look anywhere on the display screen while saccade and pupil behaviours were measured using selected features including fixation, various saccade parameters (including macrosaccades, saccade frequency, saccade rebound, vertical saccade rate), pupil constriction, pupil dilation, and vertical gaze palsy. These features are defined elsewhere in this description; vertical saccades were defined as saccades ±45° of the vertical meridian and vertical gaze palsy was defined as a significant reduction in the ability to make vertical saccades.

PD, MSA, and PSP spent more time fixating the centre of the screen than CTRL. All patient groups made fewer macrosaccades (>2° amplitude) with smaller amplitude than CTRL. Saccade frequency was greater in RBD than in other patients. Following clip change, saccades were temporarily suppressed, then rebounded at a slower pace than CTRL in all patient groups. RBD had distinct, although discrete saccade abnormalities that were more marked in PD, MSA, and even more in PSP. The vertical saccade rate was reduced in all patients and decreased most in PSP. Clip changes produced large increases or decreases in screen luminance requiring pupil constriction or dilation, respectively. PSP elicited smaller pupil constriction/dilation responses than CTRL, while MSA elicited the opposite. RBD patients already have discrete but less pronounced saccade abnormalities than PD and MSA patients. Vertical gaze palsy and altered pupil control differentiate PSP from αSYN.

Overall, the data confirm that the free viewing task together with the methods employed may be used to identify prodromal αSYN and help to distinguish early manifest αSYN from early PSP. Thus, the selected biomarkers/features that were used to identify the different neurodegenerative groups may be incorporated in a classifier in processing steps. In this example, these clinical groups are related as described above which makes the results more powerful as use of the selected features provides the ability to distinguish the groups from one another and/or predict if those with prodromal disorders such as RBD will progress to PD or MSA.

Example 5

This example describes features of eye behaviour that we have identified to be altered in various neurological disorders and may be used in structured viewing tasks and unstructured viewing tasks to detect and/or diagnose a brain disorder in a subject.

Structured Viewing Task—Features

FIG. 16 shows selected features for detecting various brain disorders (“Group”) using a structured viewing task, e.g., an interleaved pro/anti saccade task (IPAST). Other combinations of features may be selected to detect other types of brain disorders. The features are described below.

Fixation Break (Fix Break) is the percentage of trials in which subjects broke fixation during fixation.

Saccadic Reaction Time (SRT) in Pro-Saccade Trials (Pro SRT) is the latency from stimulus onset to the beginning of correct saccades in pro-saccade trials.

Express Saccades in Pro-Saccade Trials (Pro Express) is the percentage of trials in which correct pro-saccades in pro-saccade trials are initiated within the express saccade latency range (90-140 ms after stimulus onset, see FIG. 15).

SRT in Anti-Saccade Trials (Anti SRT) is the latency from stimulus onset to the beginning of correct saccades in anti-saccade trials.

Express Saccade Errors in Anti-Saccade Trials (Exp Anti Error) are the percentage of anti-saccade trials in which an erroneous saccade (e.g., saccade towards instead of away from the stimulus) was initiated within the express saccade latency range (90-140 ms after stimulus onset, see FIG. 15).

Regular Saccade Errors in Anti-Saccade Trials (Reg Anti Error) are the percentage of anti-saccade trials in which an erroneous saccade (e.g., saccade towards instead of away from the stimulus) was initiated within the regular saccade latency range (>140 ms after stimulus onset, see FIG. 15).

Pupil Baseline is the pupil size at the beginning of the fixation period (see, e.g., FIG. 14 “FIX”).

Pupil Constrict is the magnitude and velocity of pupil constriction in response to the appearance of the fixation stimulus.

Pupil Dilate is the pupil dilation following Pupil Constriction, measured as the velocity and magnitude at the time of peripheral stimulus onset.

Blinks is the blink rate during the inter-trial interval and fixation epoch (see, e.g., FIG. 14 "ITI" and "FIX", respectively).

Structured Viewing Task—Results

Patients with cerebrovascular disease (CVD) displayed increased fixation breaks, increased SRT in anti-saccade trials, increased express saccade errors, increased regular latency saccade errors, decreased pupil size at baseline, decreased pupil constriction response, and decreased pupil dilation.

Patients with behavioural variant frontotemporal dementia (bvFTD) displayed increased fixation breaks, increased frequency of express pro-saccades, increased SRT in anti-saccade trials, increased express saccade errors, increased regular latency saccade errors, decreased pupil size at baseline, decreased pupil constriction response, decreased pupil dilation, and decreased blink rate.

Patients with amyotrophic lateral sclerosis (ALS) displayed increased fixation breaks, decreased SRT in pro-saccade trials, increased frequency of express pro-saccades, increased regular latency saccade errors, and decreased pupil constriction response.

Patients with Alzheimer's disease (AD) or mild cognitive impairment (MCI) displayed increased fixation breaks, decreased SRT on pro-saccade trials, increased frequency of express pro-saccades, increased SRT in anti-saccade trials, increased express saccade errors, increased regular latency saccade errors, decreased pupil size at baseline, decreased pupil constriction response, and decreased pupil dilation.

Patients with Parkinson's disease (PARK) displayed increased fixation breaks, decreased SRT on pro-saccade trials, increased frequency of express pro-saccades, increased SRT in anti-saccade trials, increased express saccade errors, increased regular saccade errors, decreased pupil constriction response, decreased pupil dilation, and decreased blink rate.

LRRK2 gene mutation carriers (LRRK2) displayed increased fixation breaks, increased frequency of express pro-saccades, increased regular latency saccade errors, decreased pupil size at baseline, decreased pupil constriction response, and decreased pupil dilation.

Patients with Rapid Eye Movement sleep behaviour disorder (RBD) displayed decreased pupil constriction response, decreased pupil dilation, and decreased blink rate.

Patients with progressive supranuclear palsy (PSP) displayed increased fixation breaks, increased SRT in pro-saccade trials, increased SRT in anti-saccade trials, increased express saccade errors, increased regular latency saccade errors, decreased pupil size at baseline, decreased pupil constriction response, decreased pupil dilation, and increased blink rate.

Patients with Huntington's disease (HUNT) displayed increased fixation breaks, increased SRT in pro-saccade trials, increased SRT in anti-saccade trials, increased regular latency saccade errors, decreased pupil size at baseline, decreased pupil constriction response, and decreased pupil dilation.

Unstructured Viewing Task—Features

FIG. 17 shows selected features for detecting various brain disorders ("Group") using an unstructured viewing task, e.g., a free viewing task. Other combinations of features may be selected to detect other types of brain disorders. The features are described below.

Main Sequence (Main Seq) describes the relationship between saccade amplitude, saccade duration, and saccade velocity. These relationships are well-defined in healthy individuals and deviations may be a biomarker for neurological disorders.

Saccade Rebound Burst (Sacc Rebound) is the period of increased saccade rate above baseline following a brief decrease in saccade rate in response to a clip change (see, e.g., Example 2, FIG. 13, feature C).

Steady State Saccade Rate (Sacc Rate) is the rate of saccades at the time of a clip change and 1000-3000 ms after clip change (see, e.g., Example 2, FIG. 13, features A and D).

Inhibition of Microsaccades (μsacc Inhib) is the period of decreased microsaccade rate following a clip change (see, e.g., Example 2, FIG. 13, feature F).

Steady State Microsaccade Rate (μsacc Rate) is the rate of microsaccades at the time of a clip change and 1000-3000 ms after clip change (see, e.g., Example 2, FIG. 13, features E and H).

Pupil Baseline is the pupil size at the end of the previous clippet (see, e.g., Example 2, FIG. 13, features L and O).

Pupil Sensitivity is the relationship between pupil size and screen luminance.

Pupil Constrict is the magnitude of pupil constriction for the subset of clip changes that resulted in an increase in luminance.

Pupil Dilate is the magnitude of pupil dilation for the subset of clip changes that resulted in a decrease in luminance.

Steady state blink rate (Blink Rate) is the rate of blinks at the time of a clip change and 1000-3000 ms after a clip change (see, e.g., Example 2, FIG. 13, features I and K).

Transient Inhibition in blink rate (Blink Inhib) is the decrease in blink rate following a clip change (see, e.g., Example 2, feature J).

Unstructured Viewing Task—Results

Patients with cerebrovascular disease (CVD) displayed decreased saccade rate in the saccade rebound, decreased overall saccade rate, decreased microsaccade inhibition after clip change, decreased pupil constriction response, decreased pupil dilation response, increased blink rate, and decreased blink inhibition after clip changes.

Patients with behavioural variant frontotemporal dementia (bvFTD) decreased saccade rate in the saccade rebound, decreased overall saccade rate, decreased baseline pupil size, decreased pupil sensitivity to luminance, decreased pupil constriction response, decreased pupil dilation response, and increased blink rate.

Patients with amyotrophic lateral sclerosis (ALS) displayed a decrease in the slope of the main sequence (slower velocity saccades for a given amplitude), decreased microsaccade inhibition after clip changes, increased overall microsaccade rate, increased baseline pupil size, decreased pupil sensitivity to luminance, decreased pupil constriction response, decreased pupil dilation response, an increased blink inhibition after clip changes.

Patients with mild cognitive impairment (MCI) displayed decreased saccade rate in the saccade rebound, decreased overall saccade rate, decreased microsaccade inhibition after clip changes, increased overall microsaccade rate, decreased baseline pupil size, decreased pupil sensitivity to luminance, decreased pupil constriction response, decreased pupil dilation response, and increased blink rate.

Patients with Alzheimer's disease (AD) displayed decreased saccade rate in the saccade rebound, decreased overall saccade rate, decreased microsaccade inhibition after clip changes, increased overall microsaccade rate, decreased baseline pupil size, decreased pupil sensitivity to luminance, decreased pupil constriction response, decreased pupil dilation response, and increased blink rate.

Patients with Parkinson's disease (PARK) displayed decrease in the slope of the main sequence (slower velocity saccades for a given amplitude), decreased saccade rate in the saccade rebound, decreased overall saccade rate, decreased microsaccade inhibition after clip changes, increased overall microsaccade rate, increased baseline pupil size, increased pupil sensitivity to luminance, increased pupil constriction response, increased pupil dilation response, increased blink rate, and increased blink inhibition after clip changes.

Patients with multiple system atrophy (MSA) displayed decreased saccade rate in the saccade rebound, decreased overall saccade rate, decreased microsaccade inhibition after clip changes, increased overall microsaccade rate, increased baseline pupil size, increased pupil sensitivity to luminance, increased pupil constriction response, increased pupil dilation response, increased blink rate, and increased blink inhibition after clip changes.

Patients with Rapid Eye Movement sleep behaviour disorder (RBD) displayed decreased saccade rate in the saccade rebound and decreased microsaccade inhibition after clip changes.

Patients with progressive supranuclear palsy (PSP) displayed a decrease in the slope of the main sequence (slower velocity saccades for a given amplitude), decreased saccade rate in the saccade rebound, decreased overall saccade rate, decreased microsaccade inhibition after clip changes, increased overall microsaccade rate, decreased baseline pupil size, decreased pupil sensitivity to luminance, decreased pupil constriction response, decreased pupil dilation response, decreased blink rate, and decreased blink inhibition after clip changes.

Patients with Huntington's disease (HUNT) displayed a decrease in the slope of the main sequence (slower velocity saccades for a given amplitude), decreased saccade rate in the saccade rebound, increased baseline pupil size, increased pupil sensitivity to luminance, increased pupil constriction response, increased pupil dilation response, increased blink rate, and increased blink inhibition after clip changes.

General

The results reveal significant differences in the patterns of eye behaviours between the various clinical groups in both structured and unstructured viewing tasks. In particular, differences between certain groups such as between the PARK group and PSP group suggest eye tracking and analytical methods as described herein may be used to distinguish between these two disorders that are difficult to differentiate using other approaches such as symptomology rating scales.

The contents of all cited publications are incorporated herein by reference in their entirety.

EQUIVALENTS

It will be appreciated that modifications may be made to the embodiments described herein without departing from the scope of the invention. Accordingly, the invention should not be limited by the specific embodiments set forth, but should be given the broadest interpretation consistent with the teachings of the description as a whole.

REFERENCES

Al Dahhan, N. Z., Kirby, J. R., Chen, Y., Brien, D. C., and Munoz, D. P. (2020). Examining the neural and cognitive processes that underlie reading. *Eur J Neurosci.* 51:2277-2298.

Al Dahhan, N., Kirby, J. R., and Munoz, D. P. (2017). Eye movements and articulations during a letter naming speed task: children with and without dyslexia. *J. Learn. Disabilities* 50:275-285.

Calancie O G, Brien D C, Huang J, Coe B C, Booij L, Khalid-Khan S, Munoz D P. (2022) Maturation of temporal saccade prediction from childhood to adulthood: predictive saccades, reduced pupil size and blink synchronization. *J. Neurosci.* 42:69-80.

Coe, B. C., Huang, J., Brien, D. C., White, B. J., Yep, R., & Munoz, D. P. (2022). Automated Analysis Pipeline For Extracting Saccade, Pupil, and Blink Parameters Using Video-Based Eye Tracking. *bioRxiv.*

Filzmoser, P., Maronna, R., and Werner, M. (2008). Outlier identification in high dimensions. *Computational Statistics and Data Analysis,* 52:1694-1711.

Habibi, M., Oertel, W. H., White, B. J., Brien, D. C., Coe, B. C., Riek, H. C., Perkins, J., Yep, R., Itti, L., Timmermann, L., Sittig, E., Janzen, A., Munoz, D. P. (2022). Eye tracking identifies biomarkers in α-synucleinopathies versus progressive supranuclear palsy. *J. Neurology*, https://link.springer.com/article/10.1007/s00415-022-11136-5

Itti L., Koch C. (2001). Computational modelling of visual attention. *Nat Rev Neurosci,* 2:194-203.

Perkins, J. E., Janzen, A., Bernhard, F. P., Wilhelm, K., Brien, D. C., Huang, J., Coe, B. C., Vadasz, D., Mayer, G., Munoz, D. P., & Oertel, W. H. (2021). Saccade, Pupil, and Blink Responses in Rapid Eye Movement Sleep Behavior Disorder. *Movement Disorders: Official Journal of the Movement Disorder Society,* 36 (7): 1720-1726.

Peters, R. J., Iyer, A., Itti, L., & Koch, C. (2005). Components of bottom-up gaze allocation in natural images. Vision Research, 45:2397-2416.

Ramsay, J. O. and Silverman, B. W. (2002). *Applied Functional Data Analysis*, New York: Springer.

Tseng, P. H., Cameron, I. G. M., Pari, G., Reynolds, J. N., Munoz, D. P., and Itti, L. (2013). Hi-throughput classification of clinical populations from natural viewing eye movements. *J. Neurology,* 260:275-284.

Vaca-Palomares, I., Coe, B. C., Brien, D. C., Munoz, D. P., and Fernandez-Ruiz, J. (2017). Voluntary saccade inhibition deficits correlate with extended white-matter corticobasal atrophy in Huntington's disease. *Neuroimage: Clinical,* 15:502-512.

van der Maaten, L. J. P.; Hinton, G. E. (2008) Visualizing High-Dimensional Data Using t-SNE. *Journal of Machine Learning Research* 9:2579-2605.

Wang, C. A., McInnis, H., Brien, D., Pari, G., and Munoz, D. P. (2016). Disruption of pupil size modulation correlates with voluntary motor preparation deficits in Parkinson's disease. *Neuropsychologia,* 80:176-184.

Yep, R., Smorenburg, M. L., Riek, H. C., Calancie, O. G., Kirkpatrick, R. H., Perkins, J. E., Huang, J., Coe, B. C., Brien, D. C., Munoz, D. P. (2022). Interleaved pro/anti-saccade behavior across the lifespan. *Front. Aging Neurosci.* (in press).

The invention claimed is:

1. Apparatus for detecting, diagnosing, and/or assessing a brain disorder in a subject, comprising:

a display device and an eye tracker operatively connected to a processor;

wherein the display device is configured to display visual scenes to the subject according to at least one viewing task, including visual scenes selected to cause the subject to switch brain pathways used during viewing;

wherein the eye tracker is configured to track at least one of the subject's eyes during the at least one viewing task and to output eye tracking data;

wherein the processor is configured to receive the eye tracking data and to extract variation in the data that describes oculomotor measures including eye movement, eye blink, pupil behaviour, and coordination or interaction between them;

wherein the processor is configured to analyze the data for the oculomotor measures using a classifier trained to determine a brain disorder based on a pattern in the oculomotor measures, and to generate an output;

wherein the output comprises one or more of likelihood of the subject having a brain disorder, severity of the brain disorder, and a recommendation regarding consultation with a medical professional.

2. The apparatus of claim 1, wherein the at least one viewing task comprises a structured viewing task.

3. The apparatus of claim 2, wherein the structured viewing task comprises at least one of a pro-saccade task and an anti-saccade task.

4. The apparatus of claim 1, wherein the eye movement comprises one or more of saccade, smooth pursuit, and fixation.

5. The apparatus of claim 1, wherein the classifier is implemented with a machine learning model.

6. The apparatus of claim 5, wherein the machine learning model comprises a support vector machine.

7. The apparatus of claim 1, wherein the brain disorder comprises at least one of neurodegenerative disease, a neuro-developmental disorder, a neuro-atypical disorder, a psychiatric disorder, brain damage, mild cognitive impairment, amyotrophic lateral sclerosis, frontotemporal dementia, progressive supranuclear palsy, Lewy Body Dementia Spectrum, Parkinson's Disease, Alzheimer's Disease, Huntington's Disease, rapid eye movement (REM) sleep behaviour disorder, multiple system atrophy, essential tremor, vascular cognitive impairment, fetal alcohol spectrum syndrome, attention deficit hyperactivity disorder, Tourette's Syndrome, autism spectrum disorders, opsoclonus myoclonus ataxia syndrome, optic neuritis, adrenoleukodystrophy, multiple sclerosis, major depressive disorders, bipolar, an eating disorder selected from anorexia and bulimia, dyslexia, borderline personality disorder, alcohol use disorder, anxiety, neuroCOVID disorder, schizophrenia, and apnea.

8. The apparatus of claim 1, wherein the at least one viewing task comprises an unstructured viewing task.

9. The apparatus of claim 8, wherein the unstructured viewing task comprises a free viewing task.

10. A method for detecting, diagnosing, and/or assessing a brain disorder in a subject, comprising:

using a display device to present visual scenes to a subject according to at least one viewing task, including visual scenes that are selected to cause the subject to switch brain pathways used during viewing;

using an eye tracker to track at least one of the subject's eyes while the subject performs the at least one viewing task, and output eye tracking data;

using a processor to receive the eye tracking data and to extract variation in the data that describe oculomotor measures including eye movement, eye blink, pupil behaviour, and coordination or interaction between them;

wherein the processor analyzes the data for the oculomotor measures using a classifier trained to determine a brain disorder based on a pattern in the oculomotor measures, and generates an output;

wherein the output comprises one or more of likelihood of the subject having a brain disorder, severity of the brain disorder, and a recommendation regarding consultation with a medical professional.

11. The method of claim 10, wherein the at least one viewing task comprises a structured viewing task.

12. The method of claim 11, wherein the structured viewing task comprises at least one of a pro-saccade task and an anti-saccade task.

13. The method of claim 10, wherein the coordination comprises a relative rate between eye movement and eye blinks.

14. The method of claim 10, wherein the eye movement comprises one or more of saccade, smooth pursuit, and fixation.

15. The method of claim 10, wherein the classifier is implemented with a machine learning model.

16. The method of claim 15, wherein the machine learning model comprises a support vector machine.

17. The method of claim 10, wherein the brain disorder comprises at least one of neurodegenerative disease, a neuro-developmental disorder, a neuro-atypical disorder, a psychiatric disorder, brain damage, mild cognitive impairment, amyotrophic lateral sclerosis, frontotemporal dementia, progressive supranuclear palsy, Lewy Body Dementia Spectrum, Parkinson's Disease, Alzheimer's Disease, Huntington's Disease, rapid eye movement (REM) sleep behaviour disorder, multiple system atrophy, essential tremor, vascular cognitive impairment, fetal alcohol spectrum syndrome, attention deficit hyperactivity disorder, Tourette's Syndrome, autism spectrum disorders, opsoclonus myoclonus ataxia syndrome, optic neuritis, adrenoleukodystrophy, multiple sclerosis, major depressive disorders, bipolar, an eating disorder selected from anorexia and bulimia, dyslexia, borderline personality disorder, alcohol use disorder, anxiety, neuroCOVID disorder, schizophrenia, and apnea.

18. The method of claim 10, wherein the at least one viewing task comprises an unstructured viewing task.

19. The method of claim 14, wherein the unstructured viewing task comprises a free viewing task.

20. Programmed media for use with a processor, wherein the programmed media includes computer code stored on non-transitory computer readable storage media compatible with the computer, the computer code containing instructions to direct the processor to carry out processing steps comprising:

receiving eye tracking data from an eye tracker, wherein the eye tracking data are obtained from a subject during at least one viewing task comprising visual scenes that are selected to cause the subject to switch brain pathways used during viewing;

extract variation in the data that describes oculomotor measures including eye movement, eye blink, pupil behaviour, and coordination or interaction between them; and analyze the data for the oculomotor measures using a classifier trained to determine a brain disorder based on a pattern in the features of oculomotor measures, and generate an output;

wherein the output comprises one or more of likelihood of the subject having a brain disorder, severity of the brain disorder, and a recommendation regarding consultation with a medical professional.

21. The programmed media of claim 20, wherein the coordination comprises a relative rate between eye movement eye blinks; or wherein the eye movement comprises one or more of saccade, smooth pursuit, and fixation.

22. The programmed media of claim 20, wherein the classifier is implemented with a machine learning model.

* * * * *